US011542526B2

(12) United States Patent
Curiel et al.

(10) Patent No.: US 11,542,526 B2
(45) Date of Patent: Jan. 3, 2023

(54) ONCOLYTIC ADENOVIRAL VECTOR AND METHODS OF USE

(71) Applicant: Unleash Immuno Oncolytics, Inc., St. Louis, MO (US)

(72) Inventors: David T. Curiel, St. Louis, MO (US); Osvaldo Podhajcer, Ciudad Autonoma de Buenos Aires (AR); Maria Veronica Lopez, Buenos Aires (AR)

(73) Assignee: Unleash Immuno Oncolytics, Inc., St. Louis, MO (US)

( * ) Notice: Subject to any disclaimer, the term of this patent is extended or adjusted under 35 U.S.C. 154(b) by 419 days.

(21) Appl. No.: 16/797,291

(22) Filed: Feb. 21, 2020

(65) Prior Publication Data

US 2020/0270639 A1 Aug. 27, 2020

Related U.S. Application Data

(60) Provisional application No. 62/808,694, filed on Feb. 21, 2019.

(51) Int. Cl.
| *C12N 15/86* | (2006.01) |
| *A61K 39/00* | (2006.01) |
| *A61K 48/00* | (2006.01) |
| *A61K 45/06* | (2006.01) |
| *A61P 35/00* | (2006.01) |
| *C12N 7/00* | (2006.01) |
| *C07K 14/005* | (2006.01) |
| *A61K 35/761* | (2015.01) |

(52) U.S. Cl.
CPC ............ *C12N 15/86* (2013.01); *A61K 35/761* (2013.01); *A61K 45/06* (2013.01); *C07K 14/005* (2013.01); *C12N 7/00* (2013.01); *A61K 48/00* (2013.01); *C12N 2710/10022* (2013.01); *C12N 2710/10043* (2013.01)

(58) Field of Classification Search
CPC ............... A61K 2300/00; C12N 15/86; C12N 2710/10332; C12N 2710/10343; A61P 35/00
See application file for complete search history.

(56) References Cited

U.S. PATENT DOCUMENTS

| 5,543,328 A | 8/1996 | McClelland et al. |
| 5,559,099 A | 9/1996 | Wickham et al. |
| 5,712,136 A | 1/1998 | Wickham et al. |
| 5,731,190 A | 3/1998 | Wickham et al. |
| 5,756,086 A | 5/1998 | McClelland et al. |
| 5,770,442 A | 6/1998 | Wickham et al. |
| 5,801,029 A | 9/1998 | McCormick et al. |
| 5,846,782 A | 12/1998 | Wickham et al. |
| 5,856,181 A | 1/1999 | McCormick |
| 5,871,727 A | 2/1999 | Curiel |
| 5,885,808 A | 3/1999 | Spooner et al. |
| 5,922,315 A | 7/1999 | Roy |
| 5,962,311 A | 10/1999 | Wickham et al. |
| 5,965,541 A | 10/1999 | Wickham et al. |
| 5,972,706 A | 10/1999 | McCormick |
| 5,998,205 A | 12/1999 | Hallenbeck et al. |
| 6,057,155 A | 5/2000 | Wickham et al. |
| 6,127,525 A | 10/2000 | Crystal et al. |
| 6,153,435 A | 11/2000 | Crystal et al. |
| 6,194,191 B1 | 2/2001 | Zhang et al. |
| 6,225,289 B1 | 5/2001 | Kovesdi et al. |
| 6,329,190 B1 | 12/2001 | Wickham et al. |
| 6,455,314 B1 | 9/2002 | Wickham et al. |
| 6,465,253 B1 | 10/2002 | Wickham et al. |
| 6,514,943 B2 | 2/2003 | Kovesdi et al. |
| 6,576,456 B2 | 6/2003 | Wickham et al. |
| 6,649,407 B2 | 11/2003 | Wickham et al. |
| 6,740,525 B2 | 5/2004 | Roelvink et al. |
| 6,815,200 B1 | 11/2004 | Krasnykh et al. |
| 6,824,771 B1 | 11/2004 | Curiel et al. |
| 7,297,542 B2 | 11/2007 | Curiel et al. |
| 7,456,009 B2 | 11/2008 | Evans et al. |
| 8,436,160 B2 | 5/2013 | Podhajcer et al. |
| 2005/0214923 A1 | 9/2005 | Yu et al. |
| 2016/0145643 A1 | 5/2016 | Arbeit et al. |
| 2016/0317591 A1 | 11/2016 | Aboody et al. |
| 2017/0044269 A1 | 2/2017 | Curiel et al. |

(Continued)

FOREIGN PATENT DOCUMENTS

| WO | WO 96/27677 | 9/1996 |
| WO | WO 98/00524 | 1/1998 |

(Continued)

OTHER PUBLICATIONS

Alba et al., Identification of coagulation factor (F)X binding sites on the adenovirus serotype 5 hexon: effect of mutagenesis on FX interactions and gene transfer. Blood. Jul. 30, 2009;114(5):965-71.
Alderson et al., Molecular and biological characterization of human 4-1BB and its ligand. Eur J Immunol. Sep. 1994;24(9):2219-27.
Alemany et al, Blood clearance rates of adenovirus type 5 in mice. J Gen Virol. Nov. 2000;81(Pt 11):2605-2609.
Alemany et al., Complementary adenoviral vectors for oncolysis. Cancer Gene Ther. Jan.-Feb. 1999;6(1):21-5.
Ardolino et al., Cytokine treatment in cancer immunotherapy. Oncotarget. Aug. 14, 2015;6(23):19346-7.
Beatty et al., Chapter two—Adenovirus strategies for tissue-specific targeting. Adv Cancer Res. 2012;115:39-67.
Bruder et al., Modification of Ad5 hexon hypervariable regions circumvents pre-existing Ad5 neutralizing antibodies and induces protective immune responses. PLoS One. 2012;7(4):e33920. 13 pages.

(Continued)

*Primary Examiner* — Barry A Chestnut
(74) *Attorney, Agent, or Firm* — Casimir Jones, S.C.; Rikki A. Hullinger; Peter J. Schlueter

(57) ABSTRACT

Provided herein is a conditionally-replicating serotype 5 adenovirus or adenoviral vector expressing a mutant E1A protein under control of a promoter that is responsive to hypoxia and inflammation and one or more immune modulators under control of a tumor-specific promoter. The adenovirus or adenoviral vector also comprises serotype 3 fiber and hexon proteins. Also provided is a method of inducing cytotoxicity in tumor cells using a composition containing the adenovirus or adenoviral vector.

20 Claims, 18 Drawing Sheets

Specification includes a Sequence Listing.

(56) References Cited

U.S. PATENT DOCUMENTS

| | | |
|---|---|---|
| 2017/0096646 A1 | 4/2017 | Roy et al. |
| 2017/0159072 A9 | 6/2017 | Arbeit et al. |
| 2017/0202893 A1 | 7/2017 | O'Shea et al. |

FOREIGN PATENT DOCUMENTS

| | | |
|---|---|---|
| WO | WO 98/22588 | 5/1998 |
| WO | WO 99/54441 | 10/1999 |
| WO | WO 2000/034444 | 6/2000 |
| WO | WO 2003/078592 | 9/2003 |

OTHER PUBLICATIONS

Bussard et al., Tumor-associated stromal cells as key contributors to the tumor microenvironment. Breast Cancer. Aug. 11, 2016;18(1):84. 1-11.

Cameron et al., Chemokines and Their Receptors. In: Madame Curie Bioscience Database, Austin (TX): Landes Bioscience; 2000-2013. 24 pages.

Casazza et al., Tumor stroma: a complexity dictated by the hypoxic tumor microenvironment. Oncogene. Apr. 3, 2014;33(14):1743-54.

Cassetta et al., Targeting macrophages: therapeutic approaches in cancer. Nat Rev Drug Discov. Dec. 2018;17(12):887-904.

Cerullo et al., Oncolytic adenovirus coding for granulocyte macrophage colony-stimulating factor induces antitumoral immunity in cancer patients. Cancer Res. Jun. 1, 2010;70(11):4297-309.

Chen et al., Aberrant methylation of the SPARC gene promoter and its clinical implication in gastric cancer. Sci Rep. Dec. 17, 2014;4:7035. 1-9.

Chroboczek et al., The sequence of the genome of adenovirus type the sequence of the genome of adenovirus type 5 and its comparison with the genome of adenovirus type 2. Virology. Jan. 1992;186(1):280-5.

ClinicalTrials.gov Identifier NCT02760797, "A Study of Emactuzumab and RO7009789 Administered in Combination in Participants with Advanced Solid Tumors". U.S. National Library of Medicine. May 22, 2018. 9 pages.

Collin. Immune checkpoint inhibitors: a patent review (2010-2015). Expert Opin Ther Pat. May 2016;26(5):555-64.

Cong et al., The human telomerase catalytic subunit hTERT: organization of the gene and characterization of the promoter. Hum Mol Genet. Jan. 1999;8(1):137-42.

Crawford-Miksza et al., Analysis of 15 adenovirus hexon proteins reveals the location and structure of seven hypervariable regions containing serotype-specific residues. J Virol. Mar. 1996;70(3):1836-44.

Cripe et al., Fiber knob modifications overcome low, heterogeneous expression of the coxsackievirus-adenovirus receptor that limits adenovirus gene transfer and oncolysis for human rhabdomyosarcoma cells. Cancer Res. Apr. 1, 2001;61(7):2953-60. 31 pages.

Curiel et al., High-efficiency gene transfer mediated by adenovirus coupled to DNA-polylysine complexes. Hum Gene Ther. Apr. 1992;3(2):147-54.

Desjardins et al., Recurrent Glioblastoma Treated with Recombinant Poliovirus. N Engl J Med. Jul. 12, 2018;379(2):150-161.

Devaux et al., Structure of adenovirus fibre. I. Analysis of cryStructure of adenovirus fibre. I. Analysis of crystals of fibre from adenovirus serotypes 2 and 5 by electron microscopy and X-ray crystallography. J Mol Biol. Oct. 20, 1990;215(4):567-88.

Elmetwali et al., CD40 ligand induced cytotoxicity in carcinoma cells is enhanced by inhibition of metalloproteinase cleavage and delivery via a conditionally-replicating adenovirus. Mol Cancer. Mar. 8, 2010;9:52. 1-12.

Filer et al., Targeting stromal cells in chronic inflammation. Discov Med. Feb. 2007;7(37):20-6.

Forsyth et al., Oncolytic Virotherapy for Malignant Gliomas. J Clin Oncol. May 10, 2018;36(14):1440-1442.

Gall et al., Construction and characterization of hexon-chimeric adenoviruses: specification of adenovirus serotype. J Virol. Dec. 1998;72(12):10260-4.

Ghasemi et al., Selective targeting of IL-2 to NKG2D bearing cells for improved immunotherapy. Nat Commun. Sep. 21, 2016;7:12878. 1-15.

Ginsberg et al., A proposed terminology for the adenovirus antigens and virion morphological subunits. Virology. Apr. 1966;28(4):782-3.

Green et al., Biochemical studies on adenovirus multiplication. IV. Isolation, purification, and chemical analysis of adenovirus. Virology. May 1963;20:199-207.

Green et al., Evidence for a repeating cross-beta sheet structure in the adenovirus fibre. EMBO J. 1983;2(8):1357-65.

Grewal et al., CD40 and CD154 in cell-mediated immunity. Annu Rev Immunol. 1998;16:111-35.

Gubin et al., Checkpoint blockade cancer immunotherapy targets tumour-specific mutant antigens. Nature. Nov. 27, 2014;515(7528):577-81.

Hallenbeck et al., A novel tumor-specific replication-restricted adenoviral vector for gene therapy of hepatocellular carcinoma. Hum Gene Ther. Jul. 1, 1999;10(10):1721-33.

Haque et al., Worldwide increased prevalence of human adenovirus type 3 (HAdV-3) respiratory infections is well correlated with heterogeneous hypervariable regions (HVRs) of hexon. PLoS One. Mar. 28, 2018;13(3):e0194516. 13 pages.

Helin. Regulation of cell proliferation by the E2F transcription factors. Curr Opin Genet Dev. Feb. 1998;8(1):28-35.

Henry et al., Characterization of the knob domain of the adenovirus type 5 fiber protein expressed in *Escherichia coli*. J Virol. Aug. 1994;68(8):5239-46.

Horikawa et al., Cloning and characterization of the promoter region of human telomerase reverse transcriptase gene. Cancer Res. Feb. 15, 1999;59(4):826-30.

Howe et al., Effects of Ad5 E1A mutant viruses on the cell cycle in relation to the binding of cellular proteins including the retinoblastoma protein and cyclin A. Virology. Jan. 1992;186(1):15-24.

Howe et al., Evaluation of E1-mutant adenoviruses as conditionally replicating agents for cancer therapy. Mol Ther. Nov. 2000;2(5):485-95.

Howe et al., Retinoblastoma growth suppressor and a 300-kDa protein appear to regulate cellular DNA synthesis. Proc Natl Acad Sci U S A. Aug. 1990;87(15):5883-7.

International Search Report and Written Opinion for PCT/US2020/019179, dated Jun. 5, 2020, 16 pages.

Jornvall et al., The adenovirus hexon protein. The primary structure of the polypeptide and its correlation with the hexon gene. J Biol Chem. Jun. 25, 1981;256(12):6181-6.

Jounaidi et al., Conditionally replicating adenoviruses for cancer treatment. Curr Cancer Drug Targets. May 2007;7(3):285-301.

Kaliberov et al., Adenoviral targeting using genetically incorporated camelid single variable domains. Lab Invest. Aug. 2014;94(8):893-905.

Kalyuzhniy et al., Adenovirus serotype 5 hexon is critical for virus infection of hepatocytes in vivo. Proc Natl Acad Sci U S A. Apr. 8, 2008;105(14):5483-8.

Kanaya et al., hTERT is a critical determinant of telomerase activity in renal-cell carcinoma. Int J Cancer. Nov. 23, 1998;78(5):539-43.

Kimball et al., A phase I study of a tropism-modified conditionally replicative adenovirus for recurrent malignant gynecologic diseases. Clin Cancer Res. Nov. 1, 2010;16(21):5277-87.

Knipe et al., Fields Virology, 5th ed., Lippincott Williams & Wilkins, Philadelphia, Pa. 2007. TOC only. 6 pages.

Korhonen et al., Endothelial-specific gene expression directed by the tie gene promoter in vivo. Blood. Sep. 1, 1995;86(5):1828-35.

Koski et al., Treatment of cancer patients with a serotype 5/3 chimeric oncolytic adenovirus expressing GMCSF. Mol Ther. Oct. 2010;18(10):1874-84.

Krasnykh et al., Genetic targeting of an adenovirus vector via replacement of the fiber protein with the phage T4 fibritin. J Virol. May 2001;75(9):4176-83.

(56) References Cited

OTHER PUBLICATIONS

Kurihara et al., Selectivity of a replication-competent adenovirus for human breast carcinoma cells expressing the MUC1 antigen. J Clin Invest. Sep. 2000;106(6):763-71.

Kyi et al., Immune checkpoint inhibitor combinations in solid tumors: opportunities and challenges. Immunotherapy. Jun. 2016;8(7):821-37.

Kyo et al., Expression of human telomerase subunits in ovarian malignant, borderline and benign tumors. Int J Cancer. Mar. 15, 1999;80(6):804-9.

Kyo et al., Human telomerase reverse transcriptase as a critical determinant of telomerase activity in normal and malignant endometrial tissues. Int J Cancer. Jan. 5, 1999;80(1):60-3.

Kyo et al., Understanding and exploiting hTERT promoter regulation for diagnosis and treatment of human cancers. Cancer Sci. Aug. 2008;99(8):1528-38.

Laitala et al., Hypoxic Signalling in Tumour Stroma. Front Oncol. May 29, 2018;8:189. 1-13.

Lang et al., Phase I Study of DNX-2401 (Delta-24-RGD) Oncolytic Adenovirus: Replication and Immunotherapeutic Effects in Recurrent Malignant Glioma. J Clin Oncol. May 10, 2018;36(14):1419-1427.

Lawrence et al., Intracellular uncoating of type 5 adenovirus deoxyribonucleic acid. J Virol. Oct. 1967;1(5):851-67.

Lee et al., Cytokines in cancer immunotherapy. Cancers (Basel). Oct. 13, 2011;3(4):3856-93.

Liu et al., Structure of the retinoblastoma protein bound to adenovirus E1A reveals the molecular basis for viral oncoprotein inactivation of a tumor suppressor. Genes Dev. Nov. 1, 2007;21(21):2711-6.

Longo et al., Exploiting Viruses to Treat Diseases. NEJM. 2018. 379(2), 194-196.

Lopez et al., A tumor-stroma targeted oncolytic adenovirus replicated in human ovary cancer samples and inhibited growth of disseminated solid tumors in mice. Mol Ther. Dec. 2012;20(12):2222-33.

Lu et al., Transcriptional targeting of primary and metastatic tumor neovasculature by an adenoviral type 5 roundabout4 vector in mice. PLoS One. Dec. 23, 2013;8(12):e83933. 1-12.

NCBI Reference Sequence NG_007280.1. Jun. 19, 2022. 7 pages.
NCBI Reference Sequence NM_003811.4. Jul. 24, 2022. 4 pages.

Novelli et al., Deletion analysis of functional domains in baculovirus-expressed adenovirus type 2 fiber. Virology. Nov. 1991;185(1):365-76.

Okada et al., A three-kilobase fragment of the human Robo4 promoter directs cell type-specific expression in endothelium. Circ Res. Jun. 22, 2007;100(12):1712-22.

Pardoll. The blockade of immune checkpoints in cancer immunotherapy. Nat Rev Cancer. Mar. 22, 2012;12(4):252-64.

Petrova et al., The hypoxic tumour microenvironment. Oncogenesis. Jan. 24, 2018;7(1):10. 1-13.

Picarda et al., Molecular Pathways: Targeting B7-H3 (CD276) for Human Cancer Immunotherapy. Clin Cancer Res. Jul. 15, 2016;22(14):3425-3431.

Revets et al., Nanobodies as novel agents for cancer therapy. Expert Opin Biol Ther. Jan. 2005;5(1):111-24.

Roberts et al., Three-dimensional structure of the adenovirus major coat protein hexon. Science. May 30, 1986;232(4754):1148-51.

Rodriguez et al., Prostate attenuated replication competent adenovirus (ARCA) CN706: a selective cytotoxic for prostate-specific antigen-positive prostate cancer cells. Cancer Res. Jul. 1, 1997;57(13):2559-63.

Rux et al., Structural and phylogenetic analysis of adenovirus hexons by use of high-resolution x-ray crystallographic, molecular modeling, and sequence-based methods. J Virol. Sep. 2003;77(17):9553-66.

Seyama et al., Genomic structure and PCR-SSCP analysis of the human CD40 ligand gene: its application to prenatal screening for X-linked hyper-IgM syndrome. Hum Genet. Feb. 1996;97(2):180-5.

Shashkova et al., Expanded anticancer therapeutic window of hexon-modified oncolytic adenovirus. Mol Ther. Dec. 2009;17(12):2121-30.

Short et al., Substitution of adenovirus serotype 3 hexon onto a serotype 5 oncolytic adenovirus reduces factor X binding, decreases liver tropism, and improves antitumor efficacy. Mol Cancer Ther. Sep. 2010;9(9):2536-44.

Signas et al., Adenovirus 3 fiber polypeptide gene: implications for the structure of the fiber protein. J Virol. Feb. 1985;53(2):672-8.

Stewart et al., Difference imaging of adenovirus: bridging the resolution gap between X-ray crystallography and electron microscopy. EMBO J. Jul. 1993;12(7):2589-99.

Stewart et al., Image reconstruction reveals the complex molecular organization of adenovirus. Cell. Oct. 4, 1991;67(1):145-54.

Sundararajan et al., E1B 19K blocks Bax oligomerization and tumor necrosis factor alpha-mediated apoptosis. J Virol. Aug. 2001;75(16):7506-16.

Szymczak et al., Development of 2A peptide-based strategies in the design of multicistronic vectors. Expert Opin Biol Ther. May 2005;5(5):627-38.

Tai et al., SPARC in cancer biology: its role in cancer progression and potential for therapy. Drug Resist Updat. Dec. 2008;11(6):231-46.

Takakura et al., Cloning of human telomerase catalytic subunit (hTERT) gene promoter and identification of proximal core promoter sequences essential for transcriptional activation in immortalized and cancer cells. Cancer Res. Feb. 1, 1999;59(3):551-7. 23 pages.

Takakura et al., Expression of human telomerase subunits and correlation with telomerase activity in cervical cancer. Cancer Res. Apr. 1, 1998;58(7):1558-61.

Tsukuda et al., An E2F-responsive replication-selective adenovirus targeted to the defective cell cycle in cancer cells: potent antitumoral efficacy but no toxicity to normal cell. Cancer Res. Jun. 15, 2002;62(12):3438-47.

UniProtKB/Swiss-Prot Accession No. P04501. Aug. 13, 1987. 3 pages.

Vagner et al., Irresistible IRES. Attracting the translation machinery to internal ribosome entry sites. EMBO Rep. Oct. 2001;2(10):893-8.

Van Erp et al., Retargeted oncolytic adenovirus displaying a single variable domain of camelid heavy-chain-only antibody in a fiber protein. Mol Ther Oncolytics. Feb. 18, 2015;2:15001. 1-8.

Viale et al. Therapeutic Efficacy and Safety Studies of a Novel Oncolytic Adenovirus Active in Tumor-Associated Stromal Cells and Tumor Microenvironment. Cancer-Targeted Gene and Cell Therapy, May 1, 2011; 19(1), S93-S94.

Viale et al., Therapeutic improvement of a stroma-targeted CRAd by incorporating motives responsive to the melanoma microenvironment. J Invest Dermatol. Nov. 2013;133(11):2576-2584.

Vigant et al., Substitution of hexon hypervariable region 5 of adenovirus serotype 5 abrogates blood factor binding and limits gene transfer to liver. Mol Ther. Aug. 2008;16(8):1474-80.

Waddington et al., Adenovirus serotype 5 hexon mediates liver gene transfer. Cell. Feb. 8, 2008;132(3):397-409.

Wang et al., E1A induces phosphorylation of the retinoblastoma protein independently of direct physical association between the E1A and retinoblastoma products. Mol Cell Biol. Aug. 1991;11(8):4253-65.

Wold. Adenovirus Methods and Protocols. Humana Press, Totowa, NJ. 1999. TOC only. 8 pages.

Yeh et al., Human adenovirus type 41 contains two fibers. Virus Res. Aug. 1994;33(2):179-98.

Zhang et al., Human telomerase reverse transcriptase (hTERT) is a novel target of the Wnt/β-catenin pathway in human cancer. J Biol Chem. Sep. 21, 2012;287(39):32494-511.

Extended European Search Report for EP 20758769.2, dated Oct. 28, 2022, 12 pages.

Hoare, J. et al. Oncolytic virus immunotherapies in ovarian cancer: moving beyond adenoviruses. Porto Biomed J. Jun. 29, 2018;3(1):e7.

(*** = p ≤ 0.001)

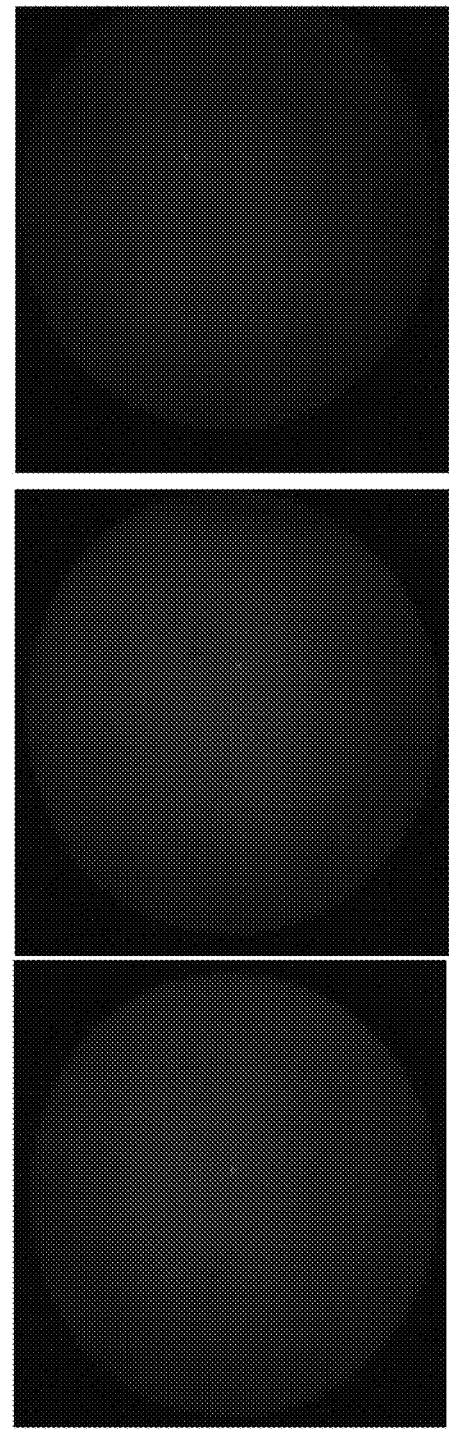
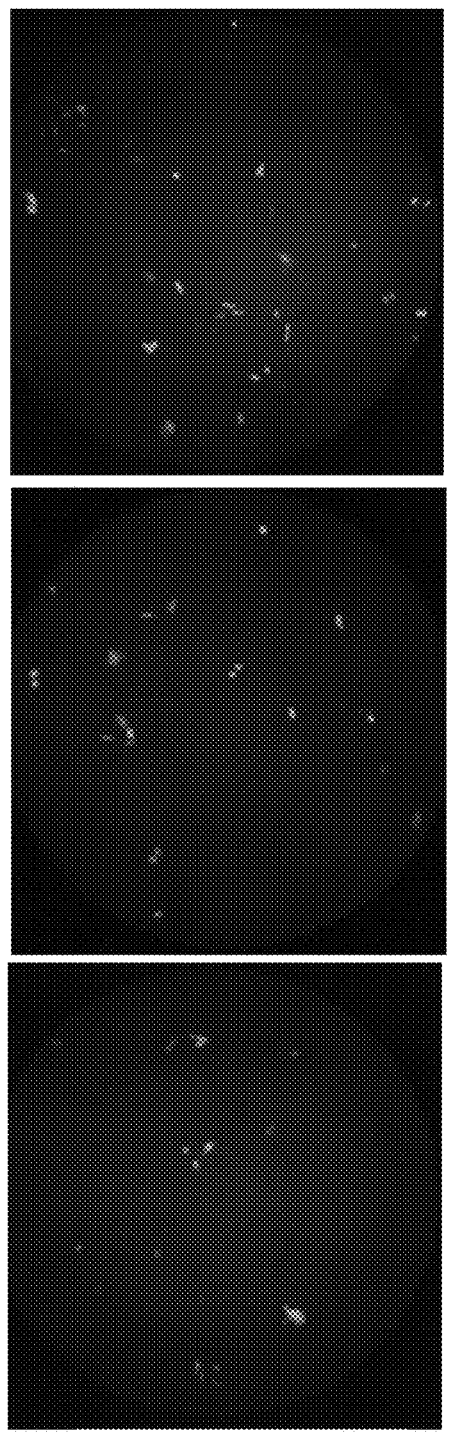

Ad.CMV-GFP.H3.F(3)

Ad.CMV-GFP.H3.F(CD276)

ONCOLYTIC ADENOVIRAL VECTOR AND METHODS OF USE

CROSS-REFERENCE TO RELATED APPLICATIONS

This application claims the benefit of U.S. Provisional Application No. 62/808,694, filed Feb. 21, 2019, the disclosure of which is incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,371 Byte ASCII (Text) file named "2020-02-21_37394-601_SQL_ST25.TXT," created on Feb. 21, 2020.

BACKGROUND OF THE INVENTION

Oncolytic virotherapy (OV) is a promising and exciting new approach for cancer treatment. Oncolytic viruses are genetically engineered or naturally occurring viruses that selectively replicate in and kill cancer cells without harming normal tissues. In addition to the primary effect of cell killing, OVs can also stimulate the immune system. Oncolytic virus immunotherapy involves the use of oncolytic viruses that also activate cells of the immune system, such as dendritic cells and T cells, and represents a promising agent for cancer immunotherapy. Current OV methodologies employ a variety of different viruses, such as adenovirus, Newcastle disease virus, herpes simplex virus, reovirus, parvovirus, and measles virus. One oncolytic virus, talimogene laherparepvec, or T-VEC (IMLYGIC™), has been approved by the FDA for local treatment of unresectable cutaneous, subcutaneous, and nodal lesions in patients with melanoma recurrent after initial surgery. Oncolytic virus immunotherapies are currently being studied in clinical trials for a variety of different cancers, such as bladder, prostate, colorectal, ovarian, lung, breast, and multiple myeloma.

With the rapid evolution of OV, methods for improving the safety and potency of oncolytic viruses are being developed, including, for example, improving tumor selectivity, enhancing infectivity and conditional replication in tumor cells, and maximizing transgene expression for enhanced cytotoxicity or host immune stimulation (see, e.g., Lang et al., *J. Clin. Oncol.*, 36; 1419-1427 (2018); Forsyth and Abate-Daga, *J. Clin. Oncol.*, 36: 1440-1442 (2018); Desjardins et al., *NEJM*, Epub Jun. 26, 2018; and Longo and Baden, *NEJM*, Epub Jun. 26, 2018).

According to the American Cancer Society (ACS), ovarian cancer ranks fifth in cancer deaths among women, accounting for more deaths than any other cancer of the female reproductive system. A woman's lifetime risk of acquiring ovarian cancer is about 1 in 78, and the lifetime chance of dying from ovarian cancer is about 1 in 108. For 2018, the ACS estimates over 22,000 ovarian cancer diagnoses and over 14,000 ovarian cancer-related deaths. The vast majority of ovarian cancers are detected at a very late stage and present with mild symptoms (e.g., hip pain). Despite improvements in therapeutic options for ovarian cancer, such as surgical cytoreduction and cytotoxic chemotherapy, there remains a need for more effective therapies, particularly for advanced disease. Oncolytic adenovirus has shown some promise targeting ovarian cancer in Phase I clinical studies (see, e.g., Kimball et al., *Clin. Cancer Res.*, 16(21): 5277-87 (2010); Cerullo et al., *Cancer Res.*, 70(11): 4297-309 (2010); and Koski et al., *Mol. Ther.*, 18(10): 1874-84 (2010)); however, the clinical response of these treatments remains unclear, and host secondary immune responses may inhibit their efficacy.

There remains a need for oncolytic virotherapy compositions and methods that exhibit improved tumor selectivity, antitumor activity, and tumor-specific host immune responses. The present disclosure provides such compositions and methods.

BRIEF SUMMARY OF THE INVENTION

The disclosure provides a serotype 5 adenovirus or adenoviral vector comprising: (a) a nucleic acid sequence encoding a mutant E1A protein operatively linked to a first promoter that is responsive to hypoxia and inflammation, (b) a deletion of all or part of the E1B region of the adenoviral genome, (c) one or more exogenous nucleic acid sequences, each of which encodes an immune modulator and is operatively linked to a second promoter that is active in tumor cells, (d) a fiber protein comprising a serotype 3 adenovirus fiber knob domain, and (e) a hexon protein comprising one or more serotype 3 hypervariable regions (HVRs).

The disclosure also provides a serotype 5 adenovirus or adenoviral vector comprising: (a) a nucleic acid sequence encoding a mutant E1A protein operatively linked to a secreted protein acidic and rich in cysteine (SPARC) promoter which comprises one or more hypoxia-responsive elements (HREs) and one or more nuclear factor kappa B (NF-κB) inflammation responsive elements (IBRE), (b) a deletion of all or part of the E1B region of the adenoviral genome, (c) a first non-native nucleic acid sequence encoding CD40 ligand (CD40L) and a second non-native nucleic acid sequence encoding 4-1BB ligand (4-1BBL), wherein the first and second non-native nucleic acid sequences are (i) separated by an internal ribosome entry site (IRES) and (ii) operatively linked to a human telomerase reverse transcriptase (hTERT) promoter, (d) a fiber protein comprising a single chain camelid antibody amino acid sequence inserted into the fiber knob, wherein the camelid antibody specifically binds to the CD276 protein, and (e) a hexon protein comprising one or more serotype 3 hypervariable regions (HVRs).

The disclosure also provides a composition comprising any of the aforementioned adenoviruses or adenoviral vectors, as well as a method of inducing cytotoxicity in tumor or cancer cells using the composition.

BRIEF DESCRIPTION OF THE DRAWING(S)

FIGS. 1A-1F are schematic diagrams illustrating several different adenovirus embodiments encompassed by the present disclosure. In particular, FIG. 1B is a schematic diagram of the UIO-523 adenovirus described in Example 1.

FIG. 2A is a plot of flow cytometric data demonstrating in vitro expression of CD40L in SKOV3 cells from isotype control (light gray), UIO-523 at MOI of 100 (intermediate gray; 33.2% positive); and UIO-523 at MOI of 1000 (dark gray; 74.8% positive). FIG. 2B is a plot of flow cytometric data demonstrating in vitro expression of CD40L in A549 cells from isotype control (light gray), UIO-523 at MOI of 100 (intermediate gray; 89.6% positive); and UIO-523 at MOI of 1000 (dark gray; 90% positive).

FIGS. 3A and 3B are graphs illustrating lytic activity of AF2011 and UIO-523 hH5 vectors in SKOV3 cells (FIG. 3A) and CT26 cells (FIG. 3B). AR2011-luc is a nonreplicating control vector. FIG. 3C is a graph illustrating the lytic activity of UIO-523 hH5, UIO-523 hH3, and UIO-523 mH3 on PA1 cells.

FIGS. 9A-9F are immunofluorescence images of CHO cells engineered to express human (CHO-hC3) or murine (CHO-mC3) CD276 on the surface following transfection with fiber-modified Ad.CMV-GFP.H3.F(CD276) (FIGS. 9D-9F) or Ad.CMV-GFP.H3.F(3) (FIGS. 9A-9C). Unmodified CHO cells served as a control.

DETAILED DESCRIPTION OF THE INVENTION

Figure 1A:
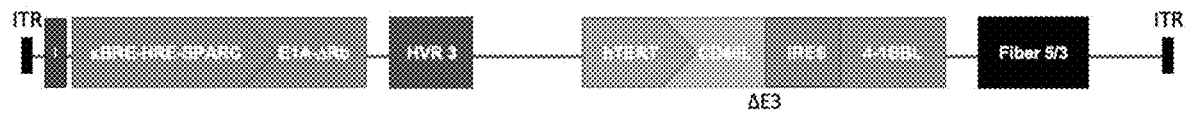

The present disclosure is predicated, at least in part, on the development of a conditionally replicative adenovirus (CRAd) that selectively replicates in tumor-associated stromal cells and expresses immune modulator proteins. The CRAd may be used in oncolytic immunotherapy applications, particularly as an adjunct to chemotherapy and/or checkpoint inhibitor therapy.

Adenovirus is a medium-sized (90-100 nm), nonenveloped icosahedral virus containing approximately 36 kilobases (kb) of double-stranded DNA. The adenovirus capsid mediates the key interactions of the early stages of the infection of a cell by the virus and is required for packaging adenovirus genomes at the end of the adenovirus life cycle. The capsid comprises 252 capsomeres, which includes 240 hexon trimers, 12 penton base pentamer proteins, and 12 trimer fibers (Ginsberg et al., *Virology*, 28: 782-83 (1966)). The hexon comprises three identical proteins, namely polypeptide II (Roberts et al., *Science*, 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell*, 67: 145-54 (1991), and Stewart et al., *EMBO J.*, 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (e.g., gene therapy, immunotherapy, or as vaccines). For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.*, 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

Over 50 serotypes of adenovirus have been identified, which are classified as subgroup A (e.g., serotypes 12, 18, and 31), subgroup B (e.g., serotypes 3, 7, 11, 14, 16, 21, 34, 35, 50, and 55), subgroup C (e.g., serotypes 1, 2, 5, and 6), subgroup D (e.g., serotypes 8, 9, 10, 13, 15, 17, 19, 20, 22-30, 32, 33, 36-39, and 42-49, 51, 53, 54, 56), subgroup E (e.g., serotype 4), subgroup F (e.g., serotypes 40 and 41), subgroup G (e.g., serotype 52). Various serotypes of adenovirus are available from the American Type Culture Collection (ATCC, Manassas, Va.).

In one embodiment, the adenovirus or adenoviral vector is a serotype 5 adenovirus or adenoviral vector ("Ad5"). The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., *Fields Virology*, 5th ed., Knipe et al. (eds.), Lippincott Williams & Wilkins, Philadelphia, Pa. (2006)). The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

In some embodiments, the adenovirus or adenoviral vector is chimeric. A "chimeric" adenovirus or adenoviral vector may comprise an adenoviral genome that is derived from two or more (e.g., 2, 3, 4, etc.) different adenovirus serotypes. In some embodiments, a chimeric adenovirus or adenoviral vector can comprise approximately equal amounts of the genome of each of the two or more different adenovirus serotypes. When the chimeric adenovirus or adenoviral vector genome is comprised of the genomes of two different adenovirus serotypes, the chimeric adenoviral vector genome preferably comprises no more than about 95% (e.g., no more than about 90%, about 85%, about 80%, about 75%, about 70%, about 65%, about 60%, about 55%, about 50%, about 45%, or about 40%) of the genome of one of the adenovirus serotypes, with the remainder of the chimeric adenovirus genome being obtained or derived from the genome of the other adenovirus serotype. In one embodiment, the majority (i.e., greater than 50%) of the genome of the adenovirus or adenoviral vector is obtained or derived from a serotype 5 adenovirus.

As discussed above, the adenovirus and adenoviral vector disclosed herein is conditionally replicating. A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific promoter. In such embodiments, replication requires the presence or absence of specific factors that activate or repress the promoter. Conditionally-replicating adenoviral vectors are further described in, e.g., U.S. Pat. Nos. 5,998,205; 6,824,771. Gene products essential for adenovirus replication are encoded by the E1, E2, and E4 regions of the adenoviral genome. The E1 region comprises the E1A and E1B subregions, while the E2 region comprises the E2A and E2B subregions. The E4 region comprises multiple open reading frames (ORFs), of which ORF6, and in some cases ORF3, are essential for adenovirus replication. The E3 region of the adenoviral genome does not include any replication-essential gene functions.

The early region 1A and 1B (E1A and E1B) genes encode proteins required for a productive adenovirus lytic cycle (Fields, supra). E1A is the first viral gene transcribed after infection and produces two related proteins, 243R and 289R, which induce transcription of the other early viral gene regions and stimulate infected cells to enter S-phase of the cell cycle. The E1B region encodes two major proteins, EIB19K and E1B55K. The E1B55K protein binds the cellular tumor suppressor p53 and can block p53-mediated apoptosis and inhibition of viral and cellular replication. The EIB19K protein is a Bcl-2 homologue that interacts with Bax and inhibits apoptosis, allowing the virus to replicate longer (Sundararajan, R and White, E, J. Virology, 75:7506-7516 (2001)). It has recently been demonstrated that the EIB proteins may not be essential for replication of oncolytic adenoviruses (Lopez et al., *Mol. Ther.,* 20: 2222-2233 (2012); and Viale et al., *J. Invest. Dermatol.,* 133(11):2576-2584 (2013)). The EIA proteins have been shown to induce S-phase in infected cells by associating with p300/CBP or the retinoblastoma (Rb) protein (Howe et al., *Proc. Natl. Acad. Sci. USA,* 87: 5883-5887 (1990); Wang et al., *Mol. Cell. Biol.,* 11: 4253-4265 (1991); Howe, J. A. and Bayley, S. T. *Virology,* 186: 15-24 (1992)). Rb and p300 regulate the activity of E2F transcription factors, which coordinate the expression of cellular genes required for cell cycle progression (Helin, K., *Curr. Opin. Genet. Dev.,* 8: 28-35 (1998)). Thus, E1A gene products play a role in viral genome replication by driving entry of quiescent cells into the cell cycle, in part, by displacing E2F transcription factors from the retinoblastoma protein (pRb) tumor suppressor (Liu, X. and Marmorstein, R, *Genes & Dev.,* 21: 2711-2716 (2007)).

Adenoviruses that conditionally replicate in certain tumor cell types typically are generated using one or a combination of the following approaches: (1) the use of tissue-specific promoters to drive expression of E1A, thereby restricting E1A-driven viral replication to specific tissues or tumors (Rodriguez et al., *Cancer Res.,* 57: 2559-2563 (1997); Alemany et al., *Cancer Gene Ther,* 6: 21-25 (1999); Hallenbeck et al., *Hum. Gene Ther.,* 10: 1721-1733 (1999); and Howe et al., *Mol. Ther.,* 2(5): 485-495 (2000)), (2) making mutations within the E1 region that abrogate viral protein interactions with either p53 or Rb to target tumor cells defective for those gene products, and/or (3) modification of native adenovirus tropism (Jounaidi et al., *Curr. Cancer Drug Targets,* 7(3): 285-301 (2007)). In one embodiment, the adenovirus or adenoviral vector described herein comprises a nucleic acid sequence encoding a mutant E1A protein. The adenovirus or adenoviral vector may comprise a nucleic acid sequence encoding any suitable mutant E1A protein, but desirably the mutant E1A protein exhibits impaired or abrogated binding to the retinoblastoma protein. The nucleic acid sequence encoding a mutant E1A protein comprises a deletion, insertion, or substitution of one or more nucleotides which renders the E A protein encoded thereby defective for Rb binding. Mutant E1A proteins which do not bind Rb, or bind to Rb with reduced affinity, are known in the art (see, e.g., U.S. Pat. Nos. 5,801,029; 5,856,181; and 5,972,706) and may be used in connection with the disclosed adenovirus or adenoviral vector. In one embodiment, the nucleic acid sequence encoding a mutant E1A protein comprises a deletion of one or more nucleotides (e.g., 1, 2, 3, 4, 5, 6, 7, 8, 9, 10 or more nucleotides) in the Rb protein binding domain of E1A. In certain embodiments, the nucleic acid sequence encoding a mutant EIA protein comprises a deletion of 10-20 nucleotides (i.e., 10, 11, 12, 13, 14, 15, 16, 17, 18, 19, or 20 nucleotides). For example, the nucleic acid sequence encoding a mutant EIA protein may comprise the nucleic acid sequence of SEQ ID NO: 1, which includes a deletion of 15 nucleotides in the Rb protein binding domain of E1A, resulting in the deletion of amino acids 123 to 127 (TCHEA) of the Rb protein binding domain of E1A.

To effect preferential replication of the adenovirus in tumor or tumor-associated cells, the nucleic acid sequence encoding the mutant E1A protein may be operatively linked to a promoter that is active in tumor cells, but not in normal cells. Such promoters are referred to herein as "tumor-specific," "tissue-specific," "cell-specific," or "cancer-specific" promoters. As used herein, the term "promoter" refers to a DNA sequence that directs the binding of RNA polymerase, thereby promoting RNA synthesis. A nucleic acid sequence is "operably linked" or "operatively linked" to a promoter when the promoter is capable of directing transcription of that nucleic acid sequence. A promoter can be native or non-native to the nucleic acid sequence to which it is operably or operatively linked. Techniques for operably linking sequences together are well known in the art. A tumor-specific or cancer-specific promoter can be chosen based upon the target tissue or tumor cell type in which the nucleic acid sequence is to be expressed. A wide variety of tumor-specific promoters have been employed in conditionally replication adenovirus constructs, any of which may be used in the context of the present disclosure. Such promoters include, for example, the α-fetoprotein promoter (Hallenbeck et al., *Hum Gene Ther,* 10 (10): 1721-33 (1999)), the prostate-specific antigen (PSA) promoter (Rodriguez et al., *Cancer Res.,* 57(13): 2559-63 (1997)), the MUC1/DF3 promoter (Kurihara et al., *J Clin Invest.,* 106: 763-771 (2000)), the human telomerase reverse transcriptase (hTERT) promoter (Zhang et al., *J Biol Chem.,* 287(39): 32494-32511 (2012)), and the E2F promoter (Tsukuda et al., *Cancer Res.,* 62; 3438-3447 (2002)).

In some embodiments, the promoter may be preferentially active in tumor or cancer cells themselves; however, in other embodiments tumor-specific or cancer-specific promoters include promoters that are preferentially active in cells that are associated with a tumor or cancer (referred to herein as "tumor-associated cells" or "cancer-associated cells"). Indeed, it will be appreciated that the tumor microenvironment is a heterogeneous population of cells consisting of the tumor bulk plus supporting (or "stroma") cells which are recruited by tumor cells from nearby endogenous host stroma. Tumor-associated stromal cells (TASCs) include, but are not limited to, vascular endothelial cells, pericytes, adipocytes, fibroblasts, and bone-marrow mesenchymal stromal cells. In certain embodiments, the nucleic acid sequence encoding the mutant E1A protein is operatively linked to a promoter that is responsive to hypoxia and inflammation, both of which are common features of tumor cells and tumor-associated stromal cells (see, e.g., Laitala, A. and J. T. Erler, *Front. Oncol.*, 8:189 (2018); Petrova et al., *Oncogenesis*, 7: 10 (2018); Casazza et al., *Oncogene*, 33(14): 1743-1754 (2014)). Indeed, TASCs are known to secrete many pro-inflammation factors, such as, IL-6, IL-8, stromal-derived factor-1 alpha, VEGF, tenascin-C and matrix metalloproteinases (Filer et al., *Discov. Med.*, 7(37): 20-26 (2007); and Bussard et al., *Breast Cancer Res.*, 18: 84 (2016)). A promoter that is responsive to hypoxia and inflammation may be engineered by incorporating one or more hypoxia response elements (HREs) and one or more inflammation response elements. In this regard, the promoter may comprise one or more (e.g., 2, 3, 4, 5, 6, 7, 8, 9, 10, or more) HREs that are responsive to hypoxia via binding the hypoxia-inducible factor-1 (HIF-1), which is a transcription factor that plays a critical role in the cell response to oxygen deficiency, and one or more (e.g., 2, 3, 4, 5, 6, 7, 8, 9, 10, or more) NF-kB inflammation response elements (kBREs).

In one embodiment, the promoter is a secreted protein acidic and rich in cysteine (SPARC) promoter. SPARC, also known as osteonectin or BM-40, is a multifaceted secreted glycoprotein which is expressed in many types of cells and is associated with tissue remodeling, wound repair, morphogenesis, cellular differentiation, cell migration, and angiogenesis. SPARC is differentially expressed in tumors and its surrounding stroma in various cancers. Higher levels of SPARC expression have been reported in breast cancer, melanomas, and glioblastomas. Lower levels of SPARC expression have been found in other types of cancers, such as ovarian, colorectal, pancreatic cancer, and acute myelogenous leukemia, primarily due to promoter methylation (Chen et al., *Scientific Reports*, 4: 7035 (2014); and Tai I. T. & Tang M. J., *Drug Resist Updat.*, 11: 231-46 (2008)). In the context of the present disclosure, the SPARC promoter is engineered to include one or more hypoxia-responsive elements (HREs) and one or more nuclear factor kappa B (NF-κB) inflammation responsive elements (KBRE), so as to direct expression of the nucleic acid sequence operatively linked thereto in tumor associated stromal cells, as discussed above. A SPARC promoter suitable for use in the disclosed adenovirus or adenoviral vector is described in, for example, U.S. Pat. No. 8,436,160.

In other embodiments, it may be desirable for the adenovirus or adenoviral vector to preferentially replicate in vascular endothelial cells (ECs), particularly tumor-associated vascular endothelial cells. Vascular endothelial cells (ECs) may be ideal targets for oncolytic virus immunotherapy as they provide widespread tissue access and are the first contact surfaces following intravenous vector administration. Thus, the nucleic acid sequence encoding the mutant E1A protein may be operatively linked to a promoter that is primarily or exclusively active in endothelial cells (i.e., an "endothelial cell-specific promoter"). Any suitable endothelial cell-specific promoter known are the art may be used, including but not limited to, an ICAM-2 promoter, an endoglin promoter, a Flt-1 promoter, a roundabout 4 (ROBO4) promoter, or a Tie1 promoter. In some embodiments, the nucleic acid sequence encoding the mutant E1A protein is operatively linked to a ROBO4 promoter (described in U.S. Patent Application Publications 2016/0145643 and 2017/0159072; Okada et al., *Circ Res.*, 100: 1712-1722 (2007); and Lu et al., *PLoS ONE*, 8(12): e83933 (2013)), or a Tie1 promoter (described in, e.g., Korhonen, *Blood*, 86(5): 1828-1835 (1995)).

In some embodiments, the adenovirus or adenoviral vector may comprise a deletion, in whole or in part, of one or more regions of the adenoviral genome. In some embodiments, the adenovirus or adenoviral vector comprises a deletion of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. For the purpose of providing sufficient space in the adenoviral genome for one or more non-native nucleic acid sequences (or "transgenes"), removal of a majority of one or more gene regions may be desirable. In this regard, the adenovirus or adenoviral vector may comprise a deletion of all or part of any of the adenoviral early regions (e.g., E1, E2, E3 and E4 regions), the late regions (e.g., the L1, L2, L3, L4, and L5 regions), genes involved in viral packaging (e.g., the IVa2 gene), and/or virus-associated RNAs (e.g., VA-RNA-1 and/or VA-RNA-2). In one embodiment, the adenovirus or adenoviral vector comprises a deletion of all or part of the E1B region of the adenoviral genome, a deletion of all or part of the E3 region of the adenoviral genome, and/or a deletion of all or part of the E4 region of the adenoviral genome. The size of the deletion may be tailored so as to retain an adenovirus or adenoviral vector whose genome closely matches the optimum genome packaging size. A larger deletion will accommodate the insertion of larger non-native nucleic acid sequences in the adenovirus or adenoviral genome.

By removing all or part of certain regions of the adenoviral genome, for example, the E1B, E3, and/or E4 regions of the adenoviral genome, the resulting adenovirus or adenoviral vector is able to accept inserts of exogenous non-native nucleic acid sequences while retaining the ability to be packaged into adenoviral capsids. Thus, in another embodiment, the adenovirus or adenoviral vector comprises one or more non-native nucleic acid sequences. A non-native nucleic acid sequence can be inserted at any position in the adenoviral genome so long as insertion allows for the formation of adenovirus or the adenoviral vector particle. A "non-native" nucleic acid sequence is any nucleic acid sequence (e.g., DNA, RNA, or cDNA sequence) that is not a naturally occurring nucleic acid sequence of an adenovirus in a naturally occurring position. Thus, a non-native nucleic acid sequence can be naturally found in an adenovirus but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the present disclosure. The non-native nucleic acid sequence preferably is DNA and preferably encodes a protein (e.g., one or more nucleic acid sequences encoding one or more proteins). The term "transgene" is defined herein as a non-native nucleic acid sequence that is operably linked to appropriate regulatory elements (e.g., a promoter), such that the non-native nucleic acid sequence can be expressed to produce an RNA or protein (e.g., a regulatory RNA sequence, peptide, or polypeptide). The regulatory elements (e.g., promoter) can be native or non-native to the adenovirus or adenoviral vector.

Each of the one or more non-native nucleic acids sequences desirably encodes an immune modulator. The terms "immune modulator," "immune modulator protein," and "immunomodulator," are used interchangeably herein and refer to a substance or protein that affects normal immune function of an organism. In some embodiments, an immune modulator stimulates immune functions of an organism, such as by activating, boosting, or restoring immune responses. In other embodiments, an immune modulator may exert a negative effect on immune function, such as by attenuating an existing immune response or preventing the stimulation of an immune response. Immune modulators may be naturally occurring substances (e.g., proteins) or may be synthetically generated compounds. Examples of naturally occurring immune modulators include, but are not limited to, cytokines, chemokines, and interleukins. Cytokines are small proteins (~25 kDa) that are released by a variety of cell types, typically in response to an activating stimulus, and induce responses through binding to specific receptors. Examples of cytokines include, but are not limited to, interferons (i.e., IFN-α, IFN-β, IFN-γ), leukemia inhibitory factor (LIF), oncostatin M (OSM), granulocyte-macrophage colony stimulating factor (GM-CSF), granulocyte colony stimulating factor (G-CSF), tumor necrosis factors (e.g., TNF-α), transforming growth factor (TGF)-β family members (e.g., TGF-β1 and TGF-β2). Chemokines are a class of cytokines that have chemoattractant properties, inducing cells with the appropriate receptors to migrate toward the source of the chemokine. Chemokines fall mainly into two groups: CC chemokines comprising two adjacent cysteines near the amino terminus, or CXC chemokines, in which two equivalent cysteine residues are separated by another amino acid. CC chemokines include, but are not limited to, chemokine ligands (CCL) 1 to 28, and CXC chemokines include, but are not limited to, CXC ligands (CXCL) 1 to 17. Interleukins are a structurally diverse group of cytokines which are secreted by macrophages in response to pathogens and include, for example, interleukin-1 (IL-1), IL-2, IL-6, IL-12, and IL-8. Other cytokines, chemokines, and interleukins are known in the art and described in e.g., Cameron M. J., and Kelvin D. J., *Cytokines, Chemokines and Their Receptors*. In: Madame Curie Bioscience Database, Austin (Tex.): Landes Bioscience; 2000-2013. Available from: www.ncbi.nlm.nih.gov/books/NBK6294/. In other embodiments, an immune modulator may be synthetically or recombinantly generated. For example, an immune modulator may be a fusion protein, a chimeric protein, or any modified version of a naturally-occurring immune modulator. Recently, a recombinant fusion protein comprised of an NKG2D ligand known as orthopoxvirus major histocompatibility complex class I like protein (OMCP) and a mutated form of IL-2 with poor affinity for IL-2Ra has been developed and may be employed in the adenovirus or adenoviral vector. This fusion protein (referred to as "OMCP-mutIL-2") potently and selectively activates IL-2 signaling only on NKG2D-bearing cells, such as natural killer (NK) cells, without broadly activating IL-2Ra-bearing cells (Ghasemi et al., *Nature Communications*, 7, Article No: 12878 (2016)).

In one embodiment, the adenovirus or adenoviral vector comprises a non-native nucleic acid sequence encoding the cytokine CD40 ligand (CD40L) and a non-native nucleic acid sequence encoding the cytokine 4-1BB ligand (4-1BBL). CD40L, also known as CDI54, is a member of the TNF protein superfamily that is primarily expressed on activated T-cells. CD40L-CD40 interaction is crucial for the in vivo priming of Th1 T cells via the stimulation of IL-12 secretion by APC (Grewal, I. S. and Flavell, R. A., *Annual Review of Immunology*, 16: 111-135 (1998)). In some embodiments, the nucleic acid sequence encoding CD40L may be mutated. For example, the non-native nucleic acid sequence may encode a CD40L that is resistant to metalloproteinase cleavage such that CD40L expression is retained at the cell membrane (as described in, e.g., Elmetwali et al., *Molecular Cancer*, 9: 52 (2010)). 4-1BB ligand, also known as CD137 ligand and TNFSF9, is a transmembrane cytokine that is part of the tumor necrosis factor (TNF) ligand family. 4-1BBL is a bidirectional signal transducer that acts as a ligand for TNFRSF9, which is a costimulatory receptor molecule in T lymphocytes. 4-1BBL is expressed by activated B cells, macrophages, dendritic cells, activated T cells, neurons, and astrocytes, and its interaction with TNFRSF9 plays a role in antigen presentation development and in the generation of cytotoxic T cells. 4-1BBR is absent from resting T lymphocytes but is rapidly expressed upon antigenic stimulation. 4-1BBL is expressed in carcinoma cell lines and is thought to be involved in T cell-tumor cell interaction. The non-native nucleic acid sequence encoding 4-1BBL may also be mutated. Nucleic acid sequences encoding CD40L and 4-1BBL are publicly available and may be used in the disclosed adenovirus or adenoviral vector (see, e.g., Seyama et al., *Hum Genet.*, 97(2): 180-5 (1996); Alderson et al., *Europ. J. Immun.*, 24: 2219-2227, 1994; NCBI Reference Sequence NG_007280.1; and NCBI Reference Sequence NM_003811.4).

In other embodiments, the adenovirus or adenoviral vector may comprise a non-native nucleic acid sequence that encodes a protein that inhibits the activity of tumor associated macrophages (TAMs). Infiltration of macrophages in solid tumors is associated with poor prognosis and chemotherapy resistance in many tumors. In mouse models of cancer, macrophages promote cancer initiation and malignant progression, and at metastatic sites macrophages promote tumor cell extravasation, survival, and growth. Thus, TAMs are being investigated as potential targets for anti-cancer therapy (Cassetta, L., and J. W. Pollard, *Nature Reviews Drug Discovery*, 17: 887-904 (2018)). In one embodiment, the non-native nucleic acid sequence may encode a protein or peptide which binds to, and inhibits signaling mediated by, the colony-stimulating factor 1 receptor (CSF1R), which is a canonical marker expressed by macrophages. For example, the non-native nucleic acid sequence may encode an antibody, or antigen-binding fragment thereof, that binds to and inhibits the activity of CSF1R. Several antibodies which specifically bind to and inhibit the activity of CSFIR are known in the art and may be encoded by the non-native nucleic acid sequence, including, for example emactuzumab (also referred to as RG-7155, see, e.g., ClinicalTrials.gov Identifier NCT02760797, "A Study of Emactuzumab and RO7009789 Administered in Combination in Participants with Advanced Solid Tumors"). Other receptors besides CSFIR that are expressed by tumor associated macrophages may be targeted by the adenovirus or adenoviral vector.

The one or more non-native nucleic acid sequences ideally are operatively linked to a second promoter that is active in tumor cells. Any suitable promoter that can direct transcription in a tumor or cancer cell may be employed. For example, the promoter may be a constitutive promoter, such as a CMV, RSV, SV40, EF2 or similar viral or mammalian promoter. More preferably the promoter is a "tumor-specific" promoter, as described herein. The one or more non-native nucleic acid sequences may be operatively linked to any tumor-specific promoter known in the art, such as those described herein. Prostate-specific antigen (PSA), cyclooxygenase-2 (Cox2), and human telomerase reverse transcriptase (TERT) promoters are examples of promoter sequences that can be used to confer selective viral replication to target tissues. In one embodiment, the one or more non-native nucleic acid sequences are operatively linked to the human telomerase reverse transcriptase (hTERT) promoter. Numerous studies have demonstrated that hTERT expression is highly specific to cancer cells and tightly associated with telomerase activity, while the other telomerase subunits are constitutively expressed both in normal and cancer cells (Takakura et al., *Cancer Res;* 58: 1558-61 (1998); Kyo et al., *Int. J Cancer,* 80: 60-3 (1999); Kanaya et al., *Int J Cancer,* 78: 539-43 (1998); Kyo et al., *Int. J Cancer,* 80: 804-9 (1999); Kyo et al., *Cancer Science,* 99(8): 1528-1538 (2008); and Zhang et al., *J Biol Chem.,* 287(39): 32494-32511 (2012)). The 5' promoter region of the hTERT gene has been characterized by several groups (see, e.g., Takakura et al., *Cancer Res.,* 59: 551-7 (1999); Horikawa et al., *Cancer Res.,* 59: 826-30 (1999); and Cong et al., *Hum Mol Genet;* 8: 137-42 (1999)), and deletion analysis of the promoter identified a 260 bp core promoter region essential for cancer-specific transcriptional activation. Within the core promoter region, several distinct transcription factor-binding sights are present, including E-boxes (CACGTG) and GC-boxes (GGGCGG).

In embodiments where the adenovirus or adenoviral vector comprises two or more non-nucleic acid sequences, the two or more non-native nucleic acid sequences may be operatively linked to the same promoter (e.g., to form a "bicistronic," "multicistronic," "or polycistronic" sequence), the two or more non-native nucleic acid sequences may be operatively linked to separate identical promoters, or the two or more non-native nucleic acid sequences may be operatively linked to separate and different promoters. When the adenovirus or adenoviral vector comprises a non-native nucleic acid sequence encoding CD40L and a non-native nucleic acid sequence encoding 4-1BBL, both nucleic acid sequences may be operatively linked to the same tumor-specific promoter. When two or more nucleic acid sequences are operatively linked to a single promoter, the nucleic acid sequences desirably are separated by an internal ribosomal entry site (IRES) or a 2A peptide (or 2A peptide-like) sequence. IRESs allow for uncoupling of translation of each coding sequence thereby avoiding the generation of inactive proteins and incorrect subcellular targeting. Promoter interference or suppression also are alleviated through the use of IRESs (see, e.g., Vagner et al., *EMBO Rep.,* 2: 893-898 (2001)). 2A self-cleaving peptides were first identified in Picornaviruses as an oligopeptide (usually 19-22 amino acids) located between two proteins in some members of the picornavirus family. 2A peptides have since been identified in other viruses. Advantages of using 2A peptides for multicistronic gene expression include, for example, their small size and their ability for efficient coexpression of genes that are placed between them. Indeed, genes placed downstream of different 2A peptide sequences can induce higher levels of expression as compared to IRESs (see, e.g., Szymczak, A. L. & Vignali, D. A., *Expert Opin Biol Ther.,* 5: 627-638 (2005)).

In certain embodiments, the adenovirus or adenoviral vector comprises at least one modified capsid protein. The adenovirus capsid mediates the key interactions of the early stages of the infection of a cell by the virus and is required for packaging adenovirus genomes at the end of the adenovirus life cycle. The capsid comprises 252 capsomeres, which includes 240 hexons, 12 penton base proteins, and 12 fibers (Ginsberg et al., *Virology,* 28: 782-83 (1966)). In one embodiment, one or more capsid proteins (also referred to herein as "coat" proteins) of the adenovirus or adenoviral vector can be manipulated to alter the binding specificity or recognition of the virus or vector for a receptor on a potential host cell. It is well known in the art that almost immediately after intravenous administration, adenovirus vectors are predominantly sequestered by the liver, with clearance of Ad5 from the bloodstream and accumulation in the liver occurring within minutes of administration (Alemany et al., *J. Gen. Virol.,* 81: 2605-2609 (2000)). Liver sequestration of adenovirus is primarily due to the abundance of the native coxsackie and adenovirus receptor (CAR) on hepatocytes. Thus, the manipulation of capsid proteins may broaden the range of cells infected by the adenovirus or adenoviral vector or enable targeting of the adenoviral vector to a specific cell type. For example, one or more capsid proteins may be manipulated so as to target the adenovirus or adenoviral vector protein to tumor cells or tumor-associated cells. Such manipulations can include deletions of the fiber, hexon, and/or penton proteins (in whole or in part), insertions of various native or non-native ligands into portions of the capsid proteins, and the like.

In some embodiments, the adenovirus or adenoviral vector comprises a modified fiber protein. The adenovirus fiber protein is a homotrimer of the adenoviral polypeptide IV that has three domains: the tail, shaft, and knob. (Devaux et al., *J. Molec. Biol.,* 215: 567-88 (1990), Yeh et al., *Virus Res.,* 33: 179-98 (1991)). The fiber protein mediates primary viral binding to receptors on the cell surface via the knob and the shaft domains (Henry et al., *J. Virol.,* 68(8): 5239-46 (1994)). The amino acid sequences for trimerization are located in the knob, which appears necessary for the amino terminus of the fiber (the tail) to properly associate with the penton base (Novelli et al., *Virology,* 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.,* 2: 1357-65 (1983), Chroboczek et al., *Virology,* 186: 280-85 (1992), and Signas et al., *J. Virol.,* 53: 672-78 (1985)). Thus, the fiber protein has multiple functions key to the life cycle of adenovirus.

The fiber protein is "modified" in that it comprises a non-native amino acid sequence in addition to or in place of a wild-type fiber amino acid sequence of the serotype 5 adenovirus or adenoviral vector. Serotype 5 adenovirus entry into cells is mediated by an initial binding step to its primary receptor, the coxsackie and adenovirus receptor (CAR). CAR exhibits reduced expression on the surface of many neoplastic cells, however. In contrast, most cells express high levels of the receptors for serotype 3 adenovirus, CD46 and Desmoglein-2 (DSG-2). Thus, modification of the serotype 5 adenovirus fiber protein has been shown to substantially improve infectivity for human tumor cells. In one embodiment, at least a portion of the wild-type fiber protein (e.g., the fiber tail, the fiber shaft, the fiber knob, or the entire fiber protein) of the disclosed serotype 5 adenovirus or adenoviral vector desirably is removed and replaced with a corresponding portion of a fiber protein from an adenovirus of a different serotype (such as those described herein). In one embodiment, the knob domain of the fiber protein of the disclosed serotype 5 adenovirus or adenoviral vector is removed and replaced with a corresponding fiber knob domain of a different adenovirus serotype. For example, the fiber protein of the serotype 5 adenovirus or adenoviral vector described may comprise a knob domain from a serotype 3 adenovirus. Other regions of the serotype 5 adenovirus fiber protein (i.e., the shaft and/or tail domains) may be removed and replaced with corresponding regions from other adenovirus serotypes (e.g., serotype 3). In one embodiment, the entire wild-type fiber protein of the serotype 5 adenovirus or adenoviral vector is replaced with the entire fiber protein of a serotype 3 adenovirus. Exchanging regions of serotype 5 adenovirus fiber protein for corresponding serotype 3 regions is described in, e.g., U.S. Pat. Nos. 5,846,782 and 7,297,542. Amino acid sequences of adenovirus serotype 3 fiber protein have been characterized and are publicly available (see, e.g., Signiis, et al., *J Virol.,* 53(2): 672-678 (1985); and UniProtKB/Swiss-Prot Accession No. P04501).

In another embodiment, at least a portion of the wild-type fiber protein of the disclosed serotype 5 adenovirus or adenoviral vector is removed and replaced with a non-adenovirus (i.e., heterologous) amino acid sequence. For example, the knob domain of the fiber protein of the serotype 5 adenovirus or adenoviral vector may be removed and replaced with an amino acid sequence or motif that has been synthetically or recombinantly generated. A few heterologous peptides have been introduced into the fiber knob domain to re-target the adenovirus, including oligo lysine, FLAG, RGD-4C RGS(His)6, and HA epitope. Due to the rather complex structure of the fiber knob domain, however, any heterologous peptide or amino acid sequence introduced into the fiber knob should not destabilize the fiber, which would render it incapable of trimerization and, hence, non-functional. Thus, any suitable heterologous amino acid sequence may be incorporated into the fiber knob domain, so long as the fiber protein is able to trimerize. In one embodiment, the fiber knob of the adenovirus or adenoviral vector described herein is removed and replaced with a trimerization motif and a receptor-binding ligand. For example, the fiber knob of the adenovirus or adenoviral vector described herein is removed and replaced with a heterologous protein comprising the tail and two amino-terminal repeats of the shaft domain of the Ad5 fiber protein genetically fused with a truncated form of the bacteriophage T4 fibritin protein, and a ligand, as described in U.S. Pat. No. 6,815,200 and Krasnykh et al., *J. Virol.,* 75(9): 4176-4183 (2001). Other examples of heterologous proteins that can replace the fiber knob region of the adenovirus or adenoviral vector include an isoleucine trimerization motif and the neck region peptide from human lung surfactant D.

The ligand may be any suitable molecule or peptide that specifically recognizes a cell surface protein that is not a native adenovirus receptor. Examples of suitable ligands include, but are not limited to, physiological ligands, anti-receptor antibodies, and cell-specific peptides. In one embodiment, the ligand is an antibody, antibody fragment, or a derivative of an antibody. In one embodiment, the ligand is an antibody fragment. Examples of antibody fragments include, but are not limited to, (i) a Fab fragment, which is a monovalent fragment consisting of the VL, VH, CL, and CH domains, (ii) a F(ab')2 fragment, which is a bivalent fragment comprising two Fab fragments linked by a disulfide bridge at the hinge region, (iii) a Fv fragment consisting of the VL and VH domains of a single arm of an antibody, (iv) a Fab' fragment, which results from breaking the disulfide bridge of an F(ab')2 fragment using mild reducing conditions, (v) a disulfide-stabilized Fv fragment (dsFv), and (vi) a single domain antibody (sdAb), which is an antibody single variable region domain (VH or VL) polypeptide that specifically binds an antigen. In one embodiment, the ligand is a single domain antibody derived from an antibody produced by a camelid (i.e., camels and alpacas). Camelids produce nonconventional antibodies that consist of only the two heavy-chains (no light-chains) as the basis of antigen (Ag) recognition and binding, and these antibodies have been utilized in adenovirus-mediated gene therapy (Revets et al., *Expert Opin. Biol. Ther.,* 5:111-124 (2005)). Camelid sdAbs possess characteristics ideal for retargeting of adenovirus, such as cytosolic stability allowing functional incorporation into the adenovirus capsid and compatibility with phage biopanning selection to allow target cell specificity (Beatty, M. S. and D. T. Curiel, *Adv. Cancer Res.,* 115: 39-67 (2012)). Indeed, camelid sdAb fragments have been demonstrated to be robust ligands for targeting adenovirus vectors (see, e.g., Kaliberov et al., *Lab Invest.,* 94(8): 893-905 (2014); van Erp et al., *Mol. Ther. Oncolytics,* 2: 15001 (2015); and U.S. Patent Application Publication 2017/0044269). It will be appreciated that the choice of camelid single domain antibody used in the modified fiber knob domain will depend on the desired cell type for adenovirus targeting. When the adenovirus or adenoviral vector is targeted to tumor or cancer cells, as described herein, the camelid sdAb ideally specifically binds to a receptor that is aberrantly expressed on the surface of tumor or cancer cells (also referred to as "tumor-specific" or "cancer-specific" receptors). Numerous tumor- or cancer-cell specific cell surface receptors are known in the art, and include, but are not limited to, HER2/neu, estrogen receptors, biotin receptor, c(RGD-K), epidermal growth factor receptor (EGFR), endothelin receptor B, fibroblast growth factor receptor (FGFR), somatostatin receptors, vasoactive intestinal peptide (VIP) receptors, cholecystokinin (CCK) receptors, bombesin/gastrin-releasing peptide (GRP) receptors, neurotensin receptors, substance P, neuropeptide Y, α-melanocyte-stimulating hormone (α-MSH), calcitonin, endothelin, carcinoembryonic antigen (CEA), and CD276 (B7-H3).

In one embodiment, the camelid single domain antibody specifically binds to CD276 protein. CD276 is an immune checkpoint member of the B7 and CD28 families, and its expression is induced on antigen-presenting cells. CD276 plays an important role in the inhibition of T-cell function and is highly overexpressed on a wide range of human solid cancers, often correlating with both negative prognosis and poor clinical outcome in patients (Picarda et al., *Clinical Cancer Res.,* 22(14): 3425-3431 (2016)). The tumor-specific expression of CD276 may allow for systemic administration of a CD276-targeted adenovirus or adenoviral vector, while avoiding infection of normal (i.e., non-cancerous cells). In addition, CD276 is expressed on the surface of A549 cells, which are used in the art to produce conditionally-replicating adenoviruses.

In other embodiments, the fiber protein comprises a non-native amino acid sequence that binds αvβ3, αvβ5, or αvβ6 integrins. Adenoviruses displaying ligands specific for αvβ3 integrin, such as an RGD motif, infect cells with a greater number of αvβ3 integrin moieties on the cell surface compared to cells that do not express the integrin to such a degree, thereby targeting the vectors to specific cells of interest. For example, the adenovirus or adenoviral vector may comprise a chimeric fiber protein comprising a non-native amino acid sequence comprising an RGD motif including, but not limited to, CRGDC (SEQ ID NO: 2), CXCRGDCXC (SEQ ID NO: 3), wherein X represents any amino acid, and CDCRGDCFC (SEQ ID NO: 4). The RGD motif can be inserted into the adenoviral fiber knob region, preferably in an exposed loop of the adenoviral knob, such as the HI loop.

Other regions of the serotype 5 adenovirus fiber protein (i.e., the shaft and/or tail domains) may be removed and replaced with corresponding regions from other adenovirus serotypes or non-adenovirus peptides. Any suitable amino acid residue(s) of the wild-type fiber protein of the disclosed serotype 5 adenovirus or adenoviral vector can be modified or removed, so long as viral capsid assembly is not impeded.

Similarly, amino acids can be added to the fiber protein as long as the fiber protein retains the ability to trimerize. Such modified fiber proteins also are referred to as "chimeric" fiber proteins, as they comprise amino acid sequences obtained or derived from two different adenovirus serotypes.

In some embodiments, the adenovirus or adenoviral vector comprises a modified hexon protein. The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, the hexon protein is a primary target for modification to reduce neutralization of adenoviral vectors (see, e.g., Gall et al., *J. Virol.*, 72: 10260-264 (1998), and Rux et al., *J. Virol.*, 77(17): 9553-9566 (2003)). The major structural features of the hexon protein are shared by adenoviruses across serotypes, but the hexon protein differs in size and immunological properties between serotypes (Jornvall et al., *J. Biol. Chem.*, 256(12): 6181-6186 (1981)). A comparison of 15 adenovirus hexon proteins revealed that the predominant antigenic and serotype-specific regions of the hexon protein appear to be in loops 1 and 2 (i.e., LI or 11, and LII or 12, respectively), within which are seven to nine discrete hypervariable regions (HVR1 to HVR 7 or HVR9) varying in length and sequence between adenoviral serotypes (Crawford-Miksza et al., *J. Virol.*, 70(3): 1836-1844 (1996), and Bruder et al., *PLoS ONE*, 7(4): e33920 (2012)).

The hexon protein is "modified" in that it comprises a non-native amino acid sequence in addition to or in place of a wild-type hexon amino acid sequence of the serotype 5 adenovirus or adenoviral vector. The Ad5 hexon protein mediates liver sequestration of the virus (Waddington et al., *Cell*, 132: 397-409 (2008); Vigant et al., *Mol. Ther.*, 16: 1474-1480 (2008); and Kalyuzhniy et al., *Pmc. Natl. Acad. Sci. USA*, 105: 5483-5488 (2008)), and modification of the hexon protein, specifically within the hypervariable 5 (HVR5) and 7 (HVR7) regions, has been shown to mitigate the endogenous liver sequestration of serotype 5 adenovirus particles (see, e.g., Alba et al., *Blood*, 114: 965-971 (2009); Shashkova et al., *Mol. Ther.*, 17: 2121-2130 (2009); and Short et el., *Mol Cancer Ther.*, 9(9): 2536-2544 (2010)). In one embodiment, at least a portion of the wild-type hexon protein (e.g., the entire hexon protein) of the disclosed serotype 5 adenovirus or adenoviral vector desirably is removed and replaced with a corresponding portion of a hexon protein from an adenovirus of a different serotype (such as those described herein). In one embodiment, the hexon protein of the serotype 5 adenovirus or adenoviral vector comprises one or more hypervariable regions (HVRs) from an adenovirus of a different serotype. For example, the hexon protein of the serotype 5 adenovirus or adenoviral vector comprises one or more (e.g., one, two, three, four, five, six, or all seven) hypervariable regions (HVRs) from a serotype 3 or serotype 11 adenovirus. In other words, one or more of the HVRs of the hexon protein of the disclosed serotype 5 adenovirus or adenoviral vector may be removed and replaced with one or more corresponding HVRs from a serotype 3 or serotype 11 adenovirus. In one embodiment, the entire wild-type hexon protein of the serotype 5 adenovirus or adenoviral vector is replaced with the entire hexon protein of a serotype 3 or serotype 11 adenovirus.

Hexon protein amino acid sequences of multiple strains of adenovirus serotype 3 have been characterized and are publicly available (see, e.g., Haque et al., *PLoS ONE*, 13(4): e0196263. doi.org/i10.1371/journal.pone.0196263 (2018)). However, any suitable amino acid residue(s) of the wild-type hexon protein of the disclosed serotype 5 adenovirus or adenoviral vector can be modified or removed, so long as viral capsid assembly is not impeded. Similarly, amino acids can be added to the hexon protein as long as the structural integrity of the capsid is maintained. Such modified hexon proteins also are referred to as "chimeric" hexon proteins, as they comprise amino acid sequences obtained or derived from two different adenovirus serotypes.

Methods for generating modified (e.g., chimeric) adenovirus hexon and fiber proteins known in the art can be used in the context of the present disclosure. Such methods are described in, for example, U.S. Pat. Nos. 5,543,328; 5,559,099; 5,712,136; 5,731,190; 5,756,086; 5,770,442; 5,846,782; 5,871,727; 5,885,808; 5,922,315; 5,962,311; 5,965,541; 6,057,155; 6,127,525; 6,153,435; 6,329,190; 6,455,314; 6,465,253; 6,576,456; 6,649,407; 6,740,525; and 6,815,200.

The adenovirus or adenoviral described herein may be produced in cell lines suitable for propagation of conditionally replicating adenoviruses, including, for example, KB cells, HeLa cells, and A549 cells (see, e.g., Lawrence and Ginsberg, *J. Virol.*, 1: 851-867 (1967); Green and Pina, *Virology*, 20: 199-207 (1963); Wold, *Adenovirus Methods and Protocols* (Humana Press, Totowa, N.J.) (1999)). Methods for the production and purification of adenoviruses and adenoviral vectors are described in, e.g., U.S. Pat. No. 6,194,191, and International Patent Application Publications WO 99/54441, WO 98/22588, WO 98/00524, WO 96/27677, and WO 2003/078592.

Figure 1B:
Figure 1C:
Figure 1D:
Figure 1E:
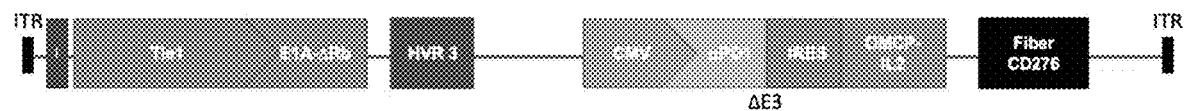
Figure 1F:
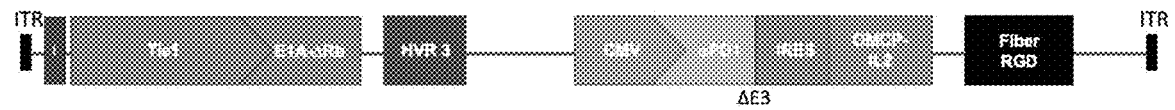

While a variety of adenoviruses or adenoviral vectors comprising various combinations of promoters, non-native nucleic acid sequences, adenoviral genome deletions, chimeric hexon proteins, and chimeric fiber proteins are encompassed by the present disclosure, particular embodiments include adenoviruses or adenoviral vectors comprising the following: (1) (a) a nucleic acid sequence encoding a mutant E1A protein operatively linked to the engineered SPARC promoter described herein that is responsive to hypoxia and inflammation, (b) a deletion of all or part of the E1B region of the adenoviral genome, (c) a nucleic acid sequence encoding CD40L and a nucleic acid sequence encoding 4-1BBL which are operatively linked to an hTERT promoter (in 5'-3' or 3'-5' orientation), (d) a fiber protein comprising a serotype 3 adenovirus fiber knob domain, and (e) a hexon protein comprising one or more serotype 3 hypervariable regions (HVRs) (see FIG. 1A and FIG. 1B); (2) (a) a nucleic acid sequence encoding a mutant E1A protein operatively linked to the engineered SPARC promoter described herein that is responsive to hypoxia and inflammation, (b) a deletion of all or part of the EIB region of the adenoviral genome, (c) a nucleic acid sequence encoding CD40L and a nucleic acid sequence encoding 4-1BBL which are operatively linked to an hTERT promoter, (d) a fiber protein comprising a non-native fiber knob domain and a CD276-specific single chain camelid antibody amino acid sequence inserted into the fiber, and (e) a hexon protein comprising one or more serotype 3 hypervariable regions (HVRs) (see FIG. 1C); (3) (a) a nucleic acid sequence encoding a mutant E1A protein operatively linked to a ROBO4 or Tie1 promoter, (b) a deletion of the E3 region of the adenoviral genome, (c) a fiber protein comprising an RGD peptide inserted into the fiber knob domain, and (d) a hexon protein comprising one or more serotype 3 hypervariable regions (HVRs) (see FIG. 1D); (4) (a) a nucleic acid sequence encoding a mutant E1A protein operatively linked to a Tie1 promoter, (b) a deletion of the E3 region of the adenoviral genome, (c) a nucleic acid sequence encoding an anti-PD1 protein (e.g., an antibody) and a nucleic acid sequence encoding OMPC-IL2 which are operatively linked to a CMV promoter, (d) a fiber protein comprising a an RGD peptide inserted into the fiber knob domain, and (e) a hexon protein comprising one or more serotype 3 hypervariable regions (HVRs) (see FIG. 1E), and (5) (a) a nucleic acid sequence encoding a mutant E1A protein operatively linked to a Tie1 promoter, (b) a deletion of the E3 region of the adenoviral genome, (c) a nucleic acid sequence encoding an anti-PD1 protein (e.g., an antibody) and a nucleic acid sequence encoding OMPC-IL2 which are operatively linked to a CMV promoter, (d) a fiber protein comprising a non-native fiber knob domain and a CD276-specific single chain camelid antibody amino acid sequence inserted into the fiber, and (e) a hexon protein comprising one or more serotype 3 hypervariable regions (HVRs) (see FIG. 1F).

The disclosure provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the disclosure, and such carriers are well known in the art. The choice of carrier will be determined, in part, by the particular use of the composition (e.g., administration to an animal) and the particular method used to administer the composition. In some embodiments, the pharmaceutical composition can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition may comprise a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector and facilitate its administration. Formulations for adenovirus or adenoviral vector-containing compositions are further described in, for example, U.S. Pat. Nos. 6,225,289, 6,514,943, and 7,456,009 and International Patent Application Publication WO 2000/034444.

In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. Antibiotics, i.e., microbicides and fungicides, can be present to treat existing infection and/or reduce the risk of future infection, such as infection associated with virus administration.

The dose of adenovirus or adenoviral vector present in the composition will depend on a number of factors, including the intended target tissue, the extent of any side-effects, the particular route of administration, and the like. The dose ideally comprises an "effective amount" of an adenovirus or adenoviral vector, i.e., a dose of adenovirus or adenoviral vector which provokes a desired response in a recipient (e.g., a human). Desirably, a single dose of adenovirus or adenoviral vector comprises at least about $1\times10^7$ particles (which also is referred to as particle units (pu) or virus particles (vp)) of the adenoviral vector. The dose is at least about $1\times10^8$ particles (e.g., about $1\times10^9$-$1\times10^{14}$ particles), and preferably at least about $1\times10^{10}$ particles, (e.g., about $1\times10^{10}$-$1\times10^{12}$ particles) of the adenovirus or adenoviral vector. Alternatively, the dose comprises no more than about $1\times10^{14}$ particles, preferably no more than about $1\times10^{13}$ particles, and more preferably no more than about $1\times10^{12}$ particles. In other words, a single dose of adenoviral vector can comprise, for example, about $1\times10^7$ virus particles, $2\times10^7$ vp, $4\times10^7$ vp, $1\times10^8$ vp, $2\times10^8$ vp, $4\times10^8$ vp, $1\times10^9$ vp, $2\times10^9$ vp, $4\times10^9$ vp, $1\times10^{10}$ vp, $2\times10^{10}$ vp, $4\times10^{10}$ vp, $1\times10^{11}$ vp, $2\times10^{11}$ vp, $4\times10^{11}$ vp, $1\times10^{12}$ vp, $2\times10^{12}$ vp, $4\times10^{12}$ vp, $1\times10^{13}$ vp, $2\times10^{13}$ vp, $4\times10^{13}$ vp, or $1\times10^{14}$ vp of the adenovirus or adenoviral vector.

The disclosure also provides method of inducing cytotoxicity in tumor cells which comprises contacting tumor cells with the above-described composition. The term "tumor," as used herein, refers to an abnormal mass of tissue that results when cells divide more than they should or do not die when they should. In the context of the present disclosure, the term tumor may refer to tumor cells and tumor-associated stromal cells (as described above). Tumors may be benign and non-cancerous if they do not invade nearby tissue or spread to other parts of the organism. In contrast, the terms "malignant tumor," "cancer," and "cancer cells" may be used interchangeably herein and refer to a tumor comprising cells that divide uncontrollably and can invade nearby tissues. Cancer cells also can spread or "metastasize" to other parts of the body through the blood and lymph systems. The disclosed method ideally induces cytotoxicity in malignant tumor cells or cancer cells. The malignant tumor cells or cancer cells may be from a carcinoma (cancer arising from epithelial cells), a sarcoma (cancer arising from bone and soft tissues), a lymphoma (cancer arising from lymphocytes), a blood cancer (e.g., myeloma or leukemia), a melanoma, or brain and spinal cord tumors. The malignant tumor or cancer cells can be located in the oral cavity (e.g., the tongue and tissues of the mouth) and pharynx, the digestive system, the respiratory system, bones and joints (e.g., bony metastases), soft tissue, the skin (e.g., melanoma), breast, the genital system, the urinary system, the eye and orbit, the brain and nervous system (e.g., glioma), or the endocrine system (e.g., thyroid) and is not necessarily the primary tumor. More particularly, cancers of the digestive system can affect the esophagus, stomach, small intestine, colon, rectum, anus, liver, gall bladder, and pancreas. Cancers of the respiratory system can affect the larynx, lung, and bronchus and include, for example, non-small cell lung carcinoma. Cancers of the reproductive system can affect the uterine cervix, uterine corpus, ovaries, vulva, vagina, prostate, testis, and penis. Cancers of the urinary system can affect the urinary bladder, kidney, renal pelvis, and ureter. Cancer cells also can be associated with lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). In one embodiment, the tumor cells are ovary cells, such as ovarian cancer cells.

An agent is "cytotoxic" and induces "cytotoxicity" if the agent (e.g., the adenovirus or adenoviral vector described herein) kills or inhibits the growth of cells, particularly cancer cells. In some embodiments, for example, cytotoxicity includes preventing cancer cell division and growth, as well as reducing the size of a tumor or cancer. Cytotoxicity of tumor cells may be measured using any suitable cell viability assay known in the art, such as, for example, assays which measure cell lysis, cell membrane leakage, and apoptosis. For example, methods including but not limited to trypan blue assays, propidium iodide assays, lactate dehydrogenase (LDH) assays, tetrazolium reduction assays, resazurin reduction assays, protease marker assays, 5-bromo-2'-deoxy-uridine (BrdU) assays, and ATP detection may be used. Cell viability assay systems that are commercially available also may be used and include, for example, CELL-TITER-GLO® 2.0 (Promega, Madison, Wis.), VIVAFIX™ 583/603 Cell Viability Assay (Bio-Rad, Hercules, Calif.); and CYTOTOX-FLUOR™ Cytotoxicity Assay (Promega, Madison, Wis.).

Ideally, the disclosed method promotes inhibition of tumor cell proliferation, the eradication of tumor cells, and/or a reduction in the size of at least one tumor such that a mammal (e.g., a human) is treated for cancer. By "treatment of cancer" is meant alleviation of cancer in whole or in part. In one embodiment, the disclosed method reduces the size of a tumor at least about 20% (e.g., at least about 25%, 30%, 35%, 40%, 45%, 50%, 55%, 60%, 65%, 70%, 75%, 80%, 85%, 90%, or 95%). Ideally, the tumor is completely eliminated.

The tumor cells may be contacted with the adenovirus composition in vitro or in vivo. the term "in vivo" refers to a method that is conducted within living organisms in their normal, intact state, while an "in vitro" method is conducted using components of an organism that have been isolated from its usual biological context. When the cell is contacted with the composition in vitro, the cell may be any suitable prokaryotic or eukaryotic cell. When the cell is contacted with the composition in vivo, the composition may be administered to an animal, such as a mammal, particularly a human, using standard administration techniques and routes. Suitable administration routes include, but are not limited to, oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. In other embodiments, the composition may be administered to a mammal using systemic delivery by intravenous, intramuscular, intraperitoneal, or subcutaneous injection.

While administration of a single dose of the adenovirus or adenoviral vector can be accomplished through a single application of the composition (e.g., a single injection to the target tissue), in other embodiments a single dose may be administered via multiple applications of the composition to different points of the target tumor, or multiple doses of the adenovirus or adenoviral vector may be administered via repeated administrations of a particular dose. The number of administrations can be from about 2 to about 50 administrations or more (including all integers between 2 and 50) over a therapeutic period. The number of administrations will depend on the tumor location, tumor size, tumor type, and the like.

The disclosed method can be performed in combination with other therapeutic methods to achieve a desired biological effect in a patient. Ideally, the disclosed method may include, or be performed in conjunction with, one or more cancer treatments. The choice of cancer treatment used in combination with the disclosed method will depend on a variety of factors, including the cancer/tumor type, stage and/or grade of the tumor or cancer, the patient's age, etc. Suitable cancer treatments that may be employed include, but are not limited, surgery, chemotherapy, radiation therapy, immunotherapy, hormone therapy, and stem cell transplantation. In one embodiment, the disclosed method further comprises treating the tumor cells with a chemotherapeutic agent. Any suitable chemotherapeutic agent can be used in the disclosed method, including, for example, adriamycin, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, floxuridine, fludarabine, fluorouracil, gemcitabine, hydroxyurea, idarubicin, ifosfamide, irinotecan, lomustine, mechlorethamine, mercaptopurine, meplhalan, methotrexate, mitomycin, mitotane, mitoxantrone, nitrosurea, paclitaxel, pamidronate, pentostatin, plicamycin, procarbazine, rituximab, streptozocin, teniposide, thioguanine, thiotepa, vinblastine, vincristine, vinorelbine, taxol, transplatinum, anti-vascular endothelial growth factor compounds ("anti-VEGFs"), anti-epidermal growth factor receptor compounds ("anti-EGFRs"), 5-fluorouracil, and the like. The type and number of chemotherapeutics used in the disclosed method will depend on the standard chemotherapeutic regimen for a particular tumor type.

In other embodiments, the disclosed method may further comprise treating the tumor or cancer cells with a cytokine, such as any of the cytokines disclosed herein. Ideally, the cytokine exhibits therapeutic efficacy against cancer (e.g., IL-2 and IFN-α) (see, e.g., Lee, S. and K. Margolin, *Cancers* (Basel), 3(4): 3856-3893 (2011); and Ardolino et al., *Oncotarget*, 6(23): 19346-19347 (2015)).

In another embodiment, the disclosed method may further comprise treating the tumor or cancer cells with an immune checkpoint regulator. Immune checkpoints are molecules on immune cells that must be activated or inhibited to stimulate immune system activity. Tumors can use such checkpoints to evade attacks by the immune system. The immune checkpoint regulator may be an antagonist of an inhibitory signal of an immune cell, also referred to as a "checkpoint inhibitor," which blocks inhibitory checkpoints (i.e., molecules that normally inhibit immune responses). For example, the immune checkpoint regulator may be an antagonist of A2AR, BTLA, B7-H3, B7-H4, CTLA4, GAL9, IDO, KIR, LAG3, PD-1, TDO, TIGIT, TIM3 and/or VISTA. Checkpoint inhibitor therapy therefore can block inhibitory checkpoints, restoring immune system function. Currently approved checkpoint inhibitors target the molecules CTLA4, PD-1, and PD-L1, and include ipilimumab (YERVOY®), nivolumab (OPDIVO®), pembrolizumab (KEYTRUDA®), atezolizumab (TECENTRIQ®), avelumab (BAVENCIO®), and durvalumab (IMFINZI®). Any suitable checkpoint inhibitor, such as those described in, e.g., Kyi, C. and M. A. Postow, *Immunotherapy*, 8(7):

821-37 (2016); Collin, M., *Expert Opin Ther Pat.*, 26(5): 555-64 (2016); Pardoll, D. M., *Nat Rev Cancer,* 12(4): 252-6 (2012); and Gubin et al., *Nature,* 515(7528): 577-81 (2014)) may be used in combination with the disclosed method. In other embodiments, the immune checkpoint regulator may be an agonist of an immune cell stimulatory receptor, such as an agonist of BAFFR, BCMA, CD27, CD28, CD40, CD122, CD137, CD226, CRTAM, GITR, HVEM, ICOS, DR3, LTBR, TACI and/or OX40. While an immune checkpoint regulator desirably is administered in a composition or formulation that is separate from a composition or formulation comprising the adenovirus or adenoviral vector, in some embodiments the adenovirus or adenoviral vector comprises a nucleic acid sequence encoding an immune checkpoint regulator. For example, the adenovirus or adenoviral vector may comprise a nucleic acid sequence encoding a PD-1 inhibitor, such as an anti-PD-1 antibody (e.g., Pembrolizumab (KEYTRUDA®), Nivolumab (OPDIVO®), or Cemiplimab (LIBTAYO®)).

The following examples further illustrate the invention but, of course, should not be construed as in any way limiting its scope.

Example 1

This example describes the construction and characterization of a serotype 5 adenovirus in accordance with the present disclosure.

UIO-523 (also referred to as AdSΔ15-40L.BBL-HV5/3-F5/3 and as UIO-522OP in U.S. Provisional Application No. 62/808,694) is a human serotype 5 conditionally replicative adenovirus (CRAd) vector (Δ15E1A, E1B−, E3+, HV5/3, F5/3) containing the DNA sequences of a SPARC promoter modified to include three hypoxia response elements (HREs) and 12 nuclear factor kappa B (NFκB) responsive elements (κBREs). The HREs serve as regulators for low oxygen environments, while the κBREs serve as a trigger for inflammation. Hypoxia and inflammation are characteristic of tumor microenvironments. The SPARC promoter is highly expressed in cancer associated fibroblast and endothelial cells in close contact with the malignant cell compartment. The modified SPARC promoter drives a mutant E1A gene encoding a protein with defective retinoblastoma (Rb) binding as discussed above. The 5' end of the viral genome has been engineered to include a chromatin insulator sequence derived from the chicken β-globin loci (cHS4), which is a naturally occurring DNA element that functionally separates differentially expressed genetic loci through its ability to block the repressive effects of heterochromatin and/or the activating effects of enhancers. Here, the insulator sequence reduces the level of background expression from the vector by blocking the effect of the viral ITR on the modified SPARC promoter.

Most of the E3 gene region of UIO-523 is intact and the serotype 5 fiber knob is replaced by the serotype 3 knob (F5/3). UIO-523 also contains a hexon protein which is exchanged for a corresponding serotype 3 sequence, which allows for reduced liver uptake upon systemic delivery. The UIO-523 vector also expresses the immune modulatory genes CD40L and 4-1BBL under the control of the cancer- and stem cell-specific hTERT promoter, which provides for tumor specific expression of cytokines. Most or all of the E1B region of the UIO-522OP genome is removed and replaced with the hTERT-CD40L/4-1BB cassette in reverse orientation compared to the original E1B transcriptional direction, and blocked by an SV40 polyA sequence to avoid interference with E1A gene transcription. UIO-523 is represented schematically in FIG. 1B.

Figure 2A:
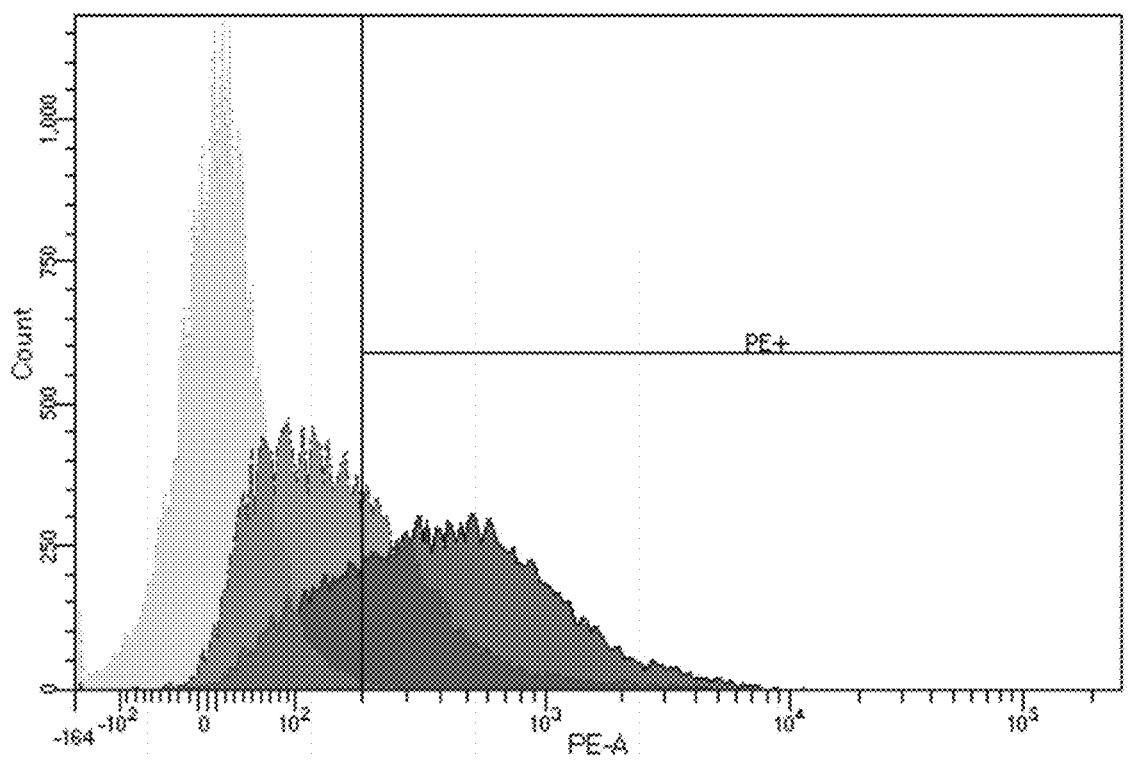
Figure 2B:
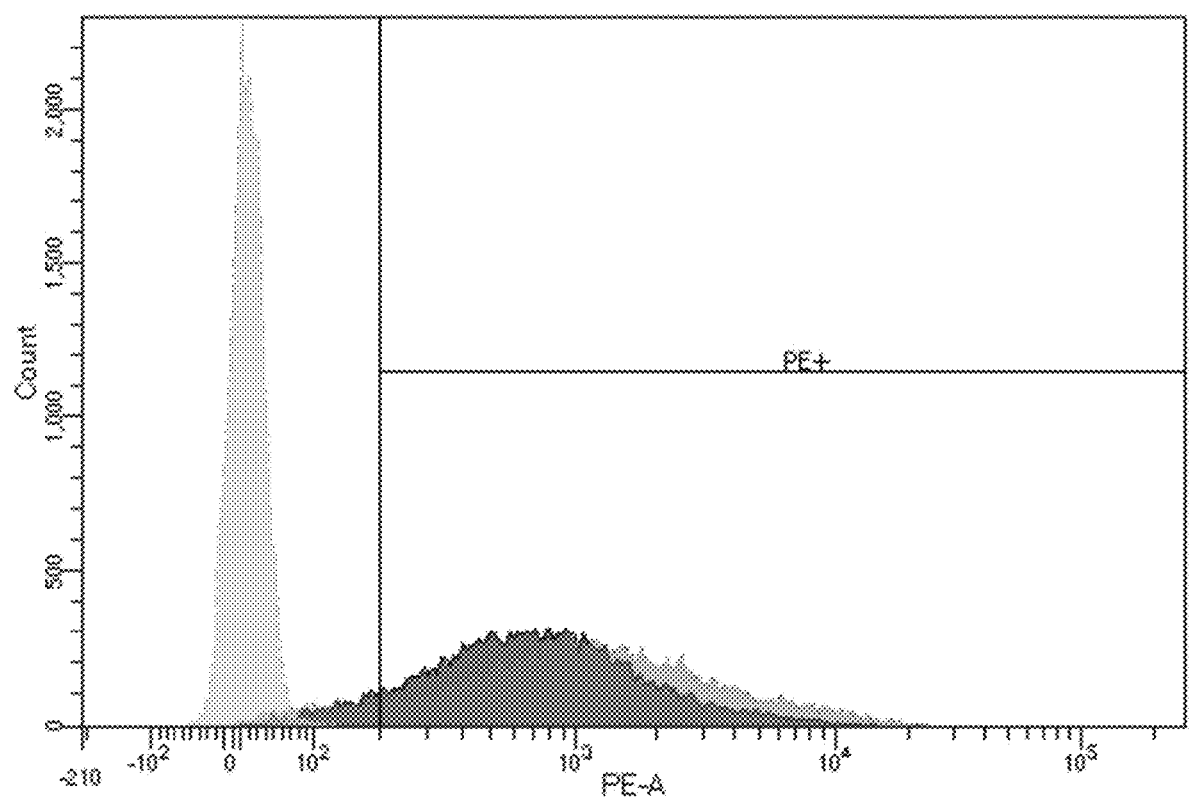
Figure 3A:
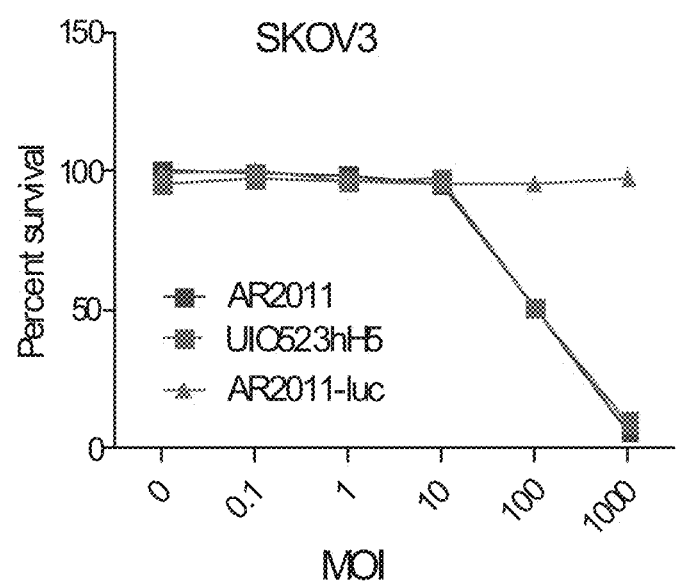
Figure 3B:
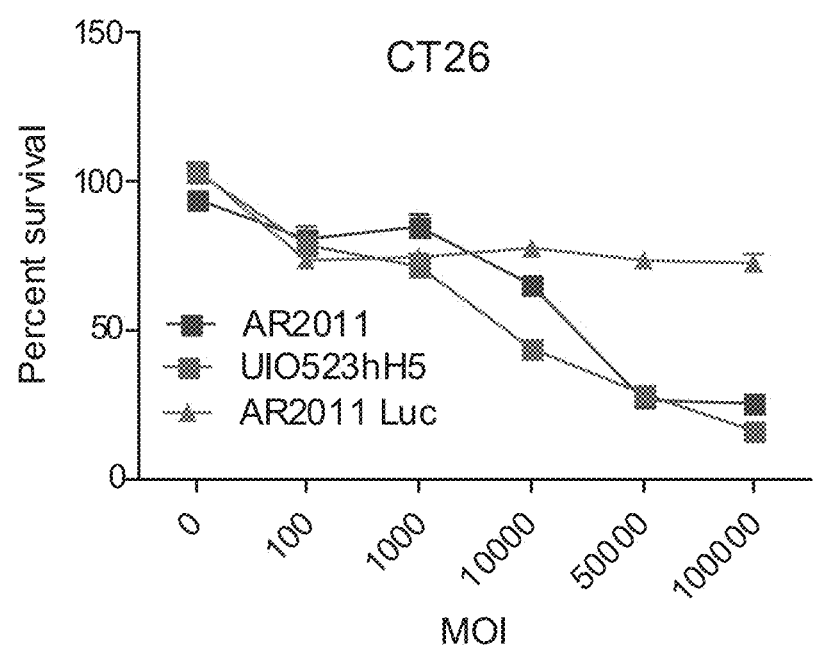
Figure 3C:
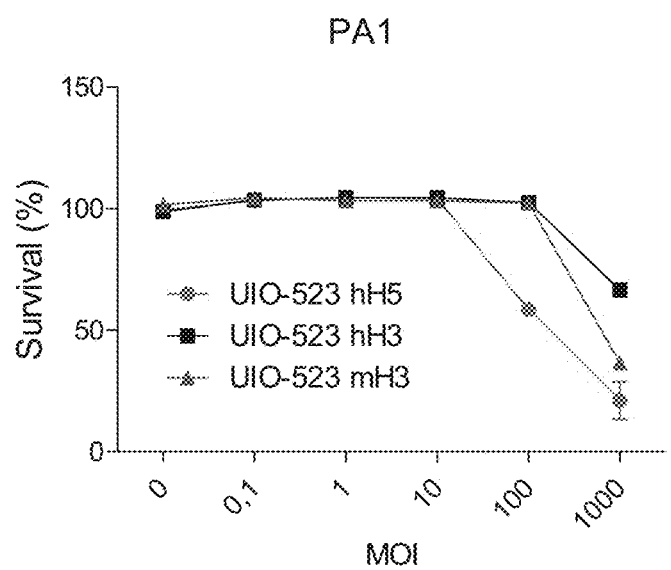

To demonstrate that UIO-523 can infect cells and produce the CD40L and 4-1BBL gene products, A549 human lung cancer cells and SKOV3 human ovary cancer cells were grown in multi-well tissue culture plates for 24 hours and infected with UIO-523, at a multiplicity of infection (MOI) of 100 or 1000. After 30 hours, cells were collected, and human CD40L was assessed by flow cytometry. The results of these studies are shown in FIGS. 2A and 2B, which demonstrate that UIO-523 can lyse cancer cells and produce cytokines to stimulate dendritic cells (DCs) and new T cells and new waves of T cells.

To evaluate the in vitro cytotoxicity of the adenoviral vectors, human ovarian cancer cells SKOV3.Luc, murine colorectal cancer CT26 cells, and PA1 human ovarian cancer cells, and were used. The viruses tested included AR2011 (unarmed virus), UIO-523 with a native serotype 5 hexon protein armed with human CD40L and 4-1BBL (UIO-523 hH5), UIO-523 having an exchange of serotype 5 hexon for serotype 3 hexon and armed with human or murine CD40L and 4-1BBL (UIO-523 hH3 or UIO-523 mH3), and AR2011-luc (non-replicating control). Cell viability was monitored with the MTT assay which measures cellular metabolic activity of NAD(P)H-dependent cellular oxidoreductase. The results of this analysis are shown in FIGS. 3A-3D. Control AR2011 virus had no lytic effect on target cells and was comparable to the activity of UIO-523 with hexon 5 expressing human cytokines on human and murine cells (see FIGS. 3A and 3B), demonstrating that adding cytokines doesn't affect the lytic activity of the virus. In addition, exchange of the hexon 5 for hexon 3 did not affect the lytic activity of UIO-523 expressing either human or murine cytokines on PA1 cells (see FIGS. 3C and 3D)

Example 2

This example describes in vivo expression of CD40L and 41BBL in a human SKOV3 ovarian cancer xenogeneic model.

6-8 week old nude mice were administered with $4.5 \times 10^6$ SKOV3.Luc cells. Once tumors reached in average 150 mm$^3$, mice were injected intratumorally (i.t.) with $1 \times 10^{10}$ v.p. per mouse or the same volume of PBS (30 μl).

Figure 4:
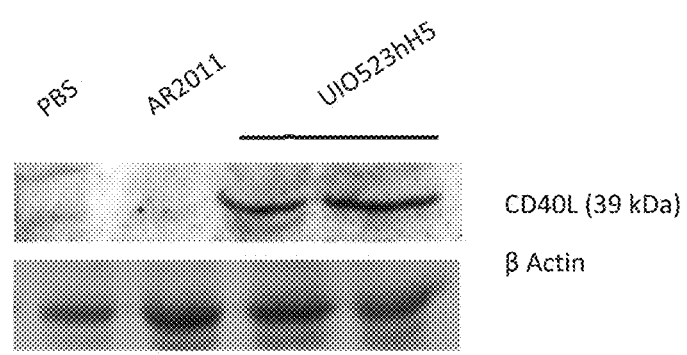
FIG. 4 is an image showing expression of CD40L in protein extracts of tumors obtained from mice treated as described in Example 2.
Figure 5A:
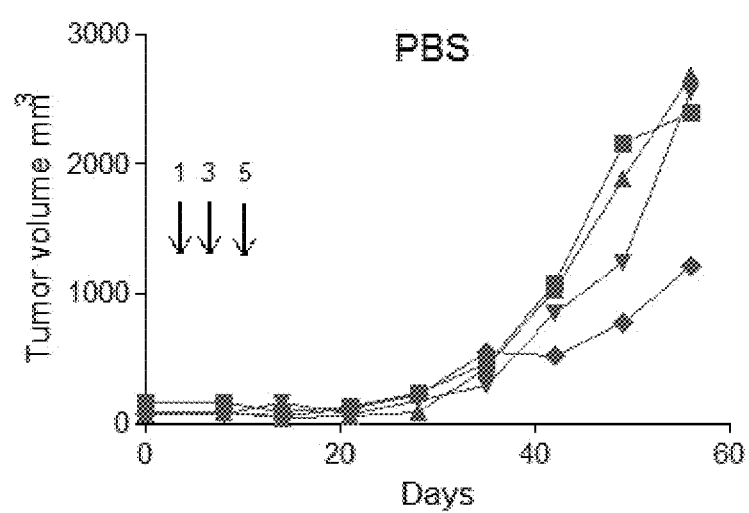
FIGS. 5A-5C are graphs illustrating tumor volume in a subcutaneous xenograft mouse model of ovarian cancer treated with PBS (FIG. 5A), AR2011 (FIG. 5B), and UIO-523 (FIG. 5C).
Figure 5B:
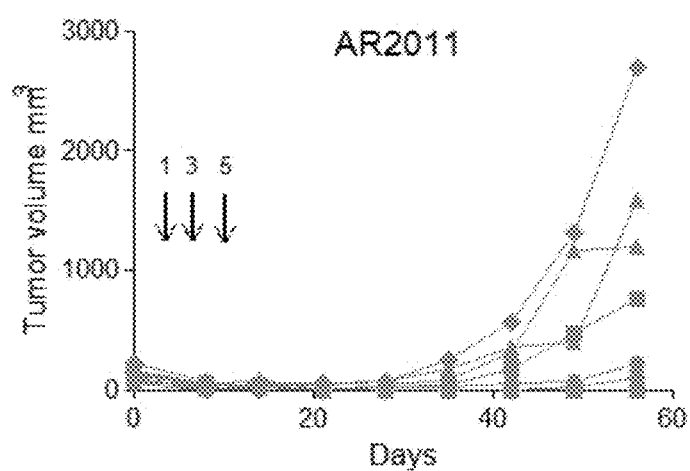
Figure 5C:
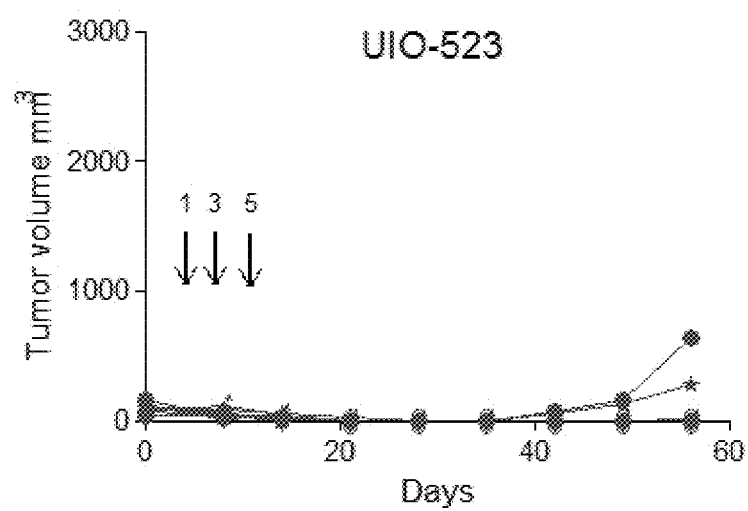
Figure 5D:
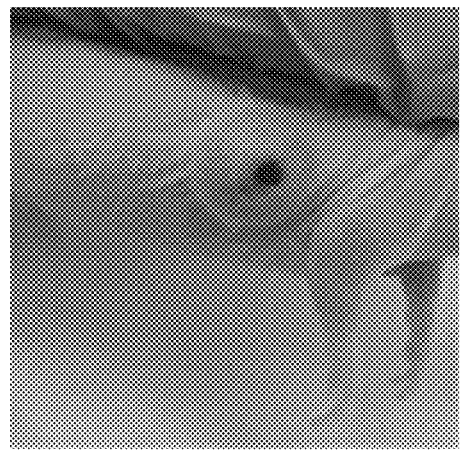
FIGS. 5D-5F are images of representative tumors in mice treated with PBS (FIG. 5D), AR2011 (FIG. 5E), and UIO-523 (FIG. 5F).
Figure 5E:
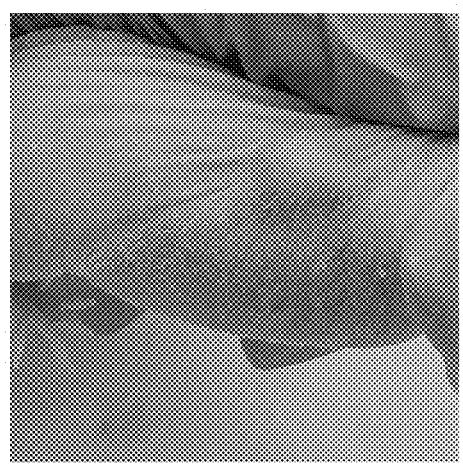
Figure 5F:
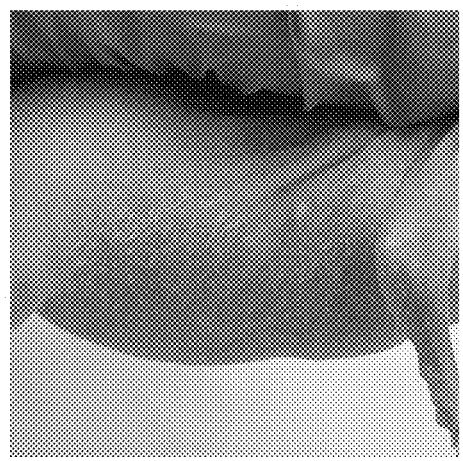

Twenty four hours later, tumors were removed and protein extracts were prepared. One hundred μg of protein extracts were separated in 12% SDS-PAGE and transferred to nitrocellulose membranes (Bio-Rad Laboratories). The membranes were probed with anti-h4-1-BBL antibody (ab68185 Abcam, Cambridge, UK) or anti-CD40L antibody (ab2391 Abcam, Cambridge, UK). Anti β-actin antibody (A4700; Sigma, St. Louis, Mo.) and anti-α tubulin (12g10 DSHB) were used as loading controls. Enhanced chemiluminescence reagents were used to detect the signals following the manufacturer's instructions (Amersham, Little Chalfont, UK). CD40L expression is show in FIG. 4. Assessment of 41BBL expression is ongoing.

Example 3

This example describes a pharmacological study of UIO-523 in a subcutaneous xenograft mouse model of ovarian cancer.

A murine xenograft model of ovarian cancer based on subcutaneous (s.c.) implantation of the human ovarian cancer cell line SKOV3 was used to evaluate UIO-523 (armed with human CD40L and 4-1BBL). Subcutaneous tumors were established by injecting 5×10⁶ SKOV3 cells/200 μL into the flanks of 6-8 week-old nude mice (n=10 mice/group). On day 10 when the tumor was established, 5×10¹⁰ vp of AR2011 or UIO-523 was injected intratumorally (i.t.) in 400 μL of PBS. PBS administration served as a negative control. Viruses were injected at days 1, 3, and 5 after tumor establishment as described (Lopez et al., *Molecular Therapy*, 20: 2222-33 (2012)). Tumor imaging was performed before treatment on day −1 and then once a week until the end of the experiment. Mice received food and water ad-libitum and were followed closely to avoid any signs of wasting or other visible indications of toxicity. Mice were sacrificed on day 45. Direct analysis of tumor reduction by imaging and animal survival were used to assess therapeutic efficacy. Complete tumor eradication was observed in mice treated with UIO-523, as shown in FIGS. 5A-5F.

Example 4

This example demonstrates the lytic activity of UIO-523 on disseminated tumors in a mouse model.

Figure 6:
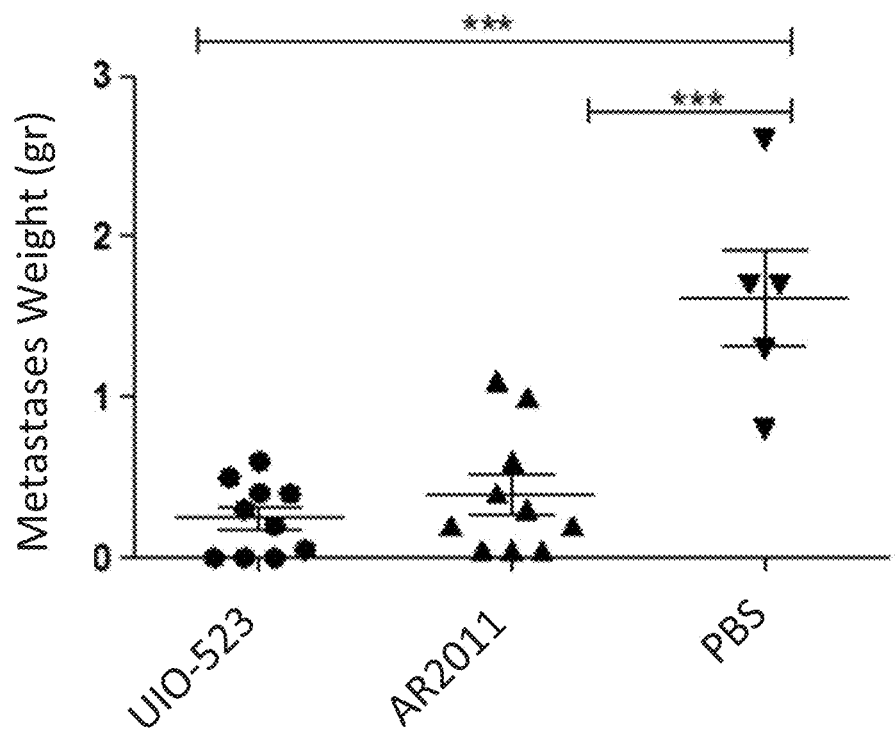
FIG. 6 is a graph illustrating the in vivo lytic activity of UIO-523 and AR2011 on disseminated tumors in an intraperitoneal mouse model of ovarian carcinomatosis.
Figure 7:
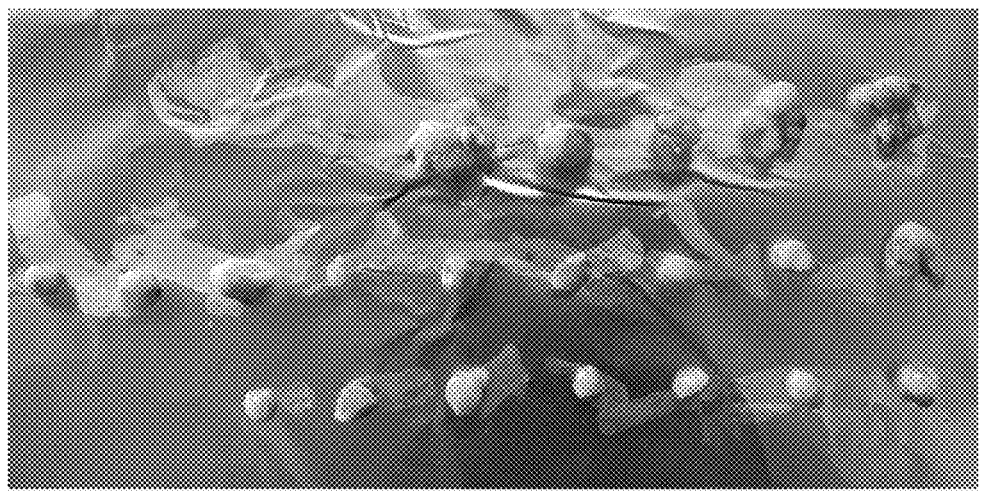
FIG. 7 is an image of excised tumors from SKOV3 intraperitoneal xenograft model mice treated with PBS control (top panel), AR2011 (middle panel), or UIO-523hH5 (bottom panel).

A murine xenograft model of ovarian cancer based on intraperitoneal implantation (i.p.) of the human ovarian cancer cell line SKOV3 was used to evaluate UIO-523 hH5 (armed with human CD40L and 4-1BBL). Intraperitoneal tumors were established by injecting 6×10⁶ SKOV3 cells into 6-8 week-old nude mice (n=10 mice/group). Seven days later, 5×10¹⁰ vp of AR2011 or UIO-523 was injected i.p. in 400 LL of PBS. PBS administration (also 400 μL) served as a negative control. Viruses were injected at days 1, 4, and 7 (Lopez et al., *Molecular Therapy*, 20: 2222-33 (2012)). Mice received food and water ad-libitum and were followed closely to avoid any signs of wasting or other visible indications of toxicity. Mice were sacrificed at day 54 after cell implantation. Statistically significant differences in tumor size were observed (see FIG. 6) and complete absence of intraperitoneal tumors was observed in several mice treated with UIO-523. Specifically, none of the mice injected with PBS were tumor free. Of the ten mice injected with UIO-523 hH5, three were tumor-free and one had a tumor ≤0.1 grams. Of the ten mice injected with AR2011, 4 had tumors ≤0.1 grams and none of the 10 mice were tumor free. Excised tumors from treated and control animals are shown in FIG. 7.

Figure 8:
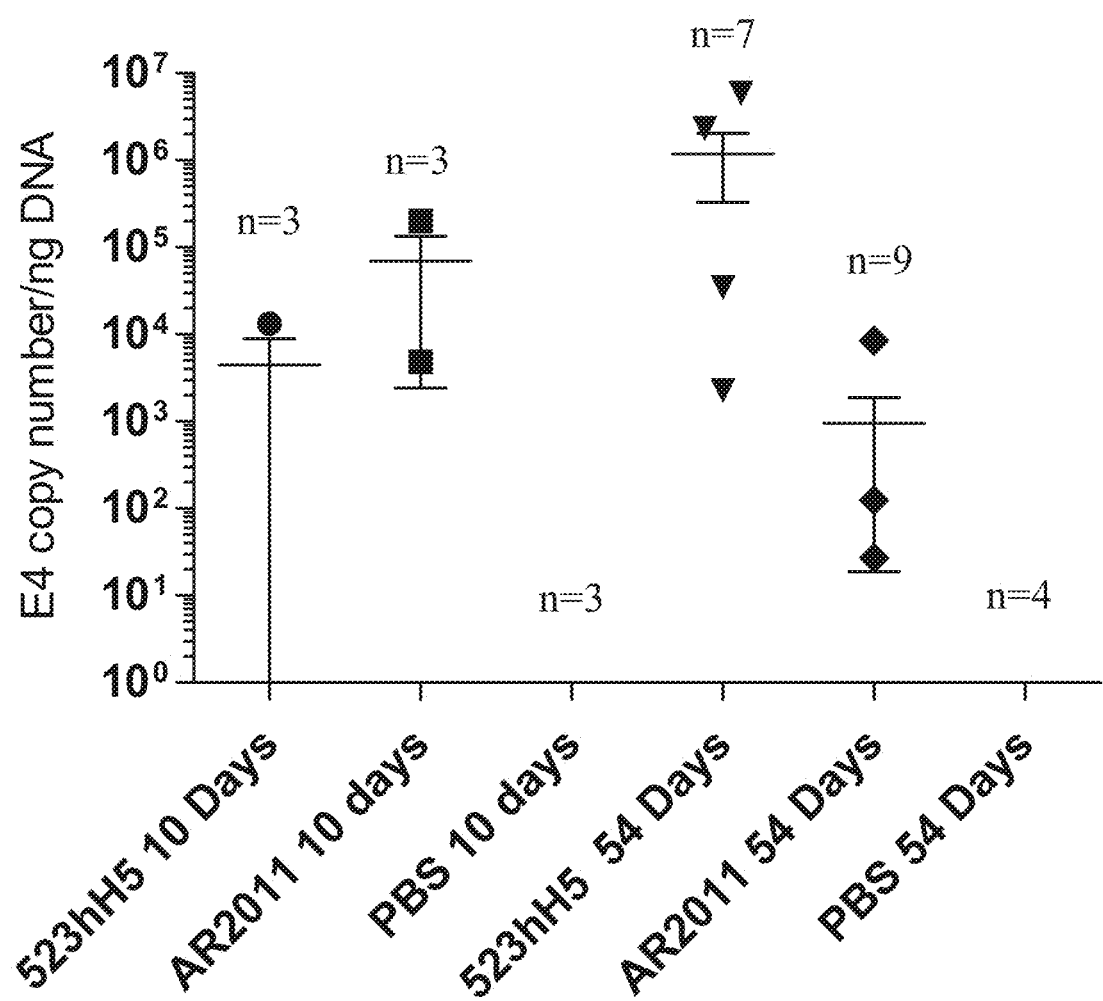
FIG. 8 is a graph showing E4 copy number/µg DNA in tumors from SKOV3 intraperitoneal xenograft model mice treated with PBS control, AR2011, or UIO-523hH5.

To assess viral distribution, total DNA was be extracted and E4 viral levels were assessed as a surrogate marker of viral particles (Lopez et al., supra). Tumors were either removed one day after the third virus administration (see FIG. 8 "10 days") or at the end of the experiment (see FIG. 8 "54 days). Viral DNA was still present at the end of the experiment, and tumors treated with UIO-523 showed higher E4 levels/μg DNA despite the fact that their tumor weight was lower.

The results of this example demonstrate that AR2011 and UIO-532 hH5 exhibited significant tumor growth suppression in the SKOV3 intraperitoneal mouse model.

Example 5

This example demonstrates the re-targeting of a conditionally-replicating adenoviral vector through fiber ablation.

As discussed herein, several strategies have been developed to alter tropism of adenoviral vectors to achieve cell-specific gene delivery by modifying the fiber protein via genetic incorporation of targeting motifs. Here, anti-CD276 single variable domains derived from a heavy chain (VHH) camelid family of antibodies were generated to achieve tumor-specific adenoviral vector gene transfer.

Figure 10A:
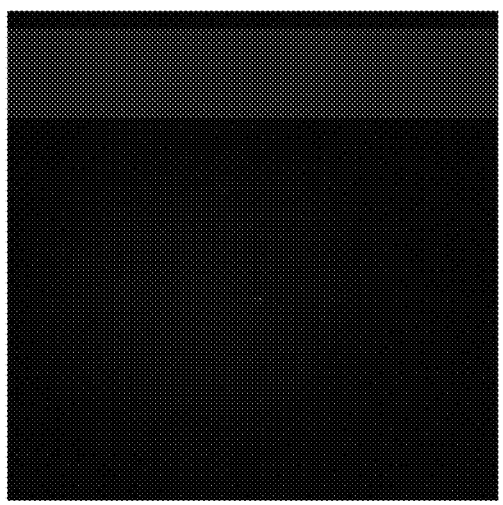
FIGS. 10A and 10B are immunofluorescence images of rhabdomyosarcoma cells infected with Ad.CMV-GFP.H3.F (3) (FIG. 10A) and Ad.CMV-GFP.H3.F(CD276) (FIG. 10B).
Figure 10B:
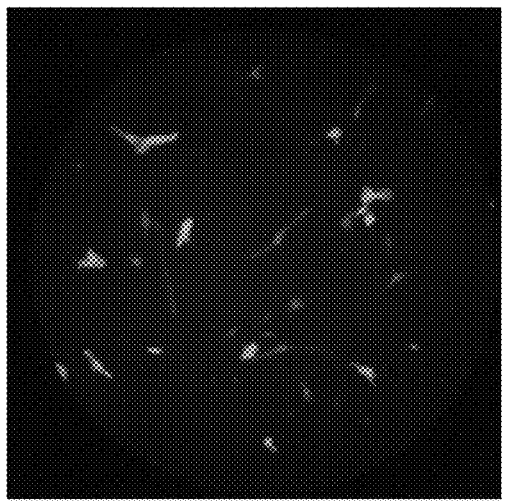

To obtain anti-CD276 VHHs, a VHH-display library was generated from peripheral blood lymphocytes RNA of alpacas at the peak of immune response to the CD276 antigen, as described in Kaliberov et al., *Laboratory Investigation*, 94: 893-905 (2014). The fiber protein of serotype 3 human adenovirus was removed and replaced with a hybrid fibritin-anti-CD276 VHH fragment to redirect the vector to the CD276 receptor (as described in Kaliberov et al., supra). The vector was also deleted in the E1 region and replaced with a CMV promoter to express green fluorescent protein (GFP), resulting in the constructs Ad.CMV-GFP.H3.F (CD276) and Ad.CMV-GFP.H3.F(3). Chinese hamster ovary (CHO) cells engineered to express human or murine CD276 on the surface were transfected with Ad.CMV-GFP.H3.F(CD276) and Ad.CMV-GFP.H3.F(3). Unmodified CHO cells served as a control. Ad.CMV-GFP.H3.F(CD276) demonstrated selective targeting to CD276 expressed on the surface of CHO cells, as shown in FIGS. 9A-9F. Ad.CMV-GFP.H3.F(CD276) also was able to infect human rhabdomyosarcoma cells, which express the adenovirus internalization receptors, $\alpha_v$ integrins, but express the major adenovirus attachment receptor, coxsackievirus-adenovirus receptor (CAR), at low or undetectable levels (Cripe et al., *Cancer Research*, 61: 2953-2960 (2001)) (see FIGS. 10A and 10B).

Example 6

This example describes a pharmacology study in a syngeneic ID8 mouse model of UIO-523.

This study will provide an efficacy assessment of UIO-523 to inhibit tumor growth of a mouse tumor cell line (ID8) in C57BL/6 mice, as well as the anti-tumor immune response. Where cytokine cross-reactivity between human and mouse is an issue, surrogate vectors were constructed with murine versions of the genes to be able to accurately determine the biological response of the arming genes. Also, F5/3 or RGD fiber will be used depending on cell line infectibility. Additional safety readouts will be built as necessary for this study.

A murine version of UIO-523 (mUIO-523) also will be studied in a syngeneic immunocompetent murine model of cancer of the ovary. This model is based on the CT26 murine colorectal cancer cell line. In this instance, the ID8 cell line will be tagged with a reporter gene allowing imaging analysis. C57BL/6 mice will be engrafted orthotopically with 5×10⁶ ID8-F3mCherryLuc cells/200 μL (n=10 mice/group). After one week, animals will be challenged i.p. with 5×10⁹ or 5×10¹⁰ vp of UIO-523. A corresponding group of mice will also be injected with virus by i.v. administration for comparison of the two different delivery routes. Direct imaging analysis on a weekly basis will allow assessment of anti-tumor effects. In addition, analysis of immunocytes derived from the peritoneal fluid and spleen by ELISPOT technology will allow a determination of the induction of anti-tumor immunity. For fidelity, murine surrogates of the arming cytokines will be employed within the viruses being studied and systemic expression levels for these genes will be measured. The study will be conducted for approximately 60 days with regular clinical observations to assess changes in animal health. Histopathology will be conducted on major organs (e.g., brain, liver, lung, kidney, heart) and the injection site area.

Example 7

This example describes a method of administering UIO-523 and a checkpoint inhibitor in a syngeneic mouse model.

C57BL/6 mice will be engrafted orthotopically with $5 \times 10^6$ ID8-F3mCherryLuc cells/200 µL (n=10 mice/group). After one week, animals will be challenged either i.p. or i.v. with $5 \times 10^9$ or $5 \times 10^{10}$ v.p. of UIO-523 (i.p. or i.v. delivery will be determined from results obtained in the initial monotherapy efficacy studies described above). On days 8 and 13, mice will be injected i.v. with 25 µg/mouse of an anti-mouse PDL1 monoclonal antibody. Direct imaging analysis will allow assessment of anti-tumor effects. In addition, analysis of immunocytes derived from the peritoneal fluid and spleen by ELISPOT technology will allow a determination of the induction of anti-tumor immunity. Survival of the treatment groups will be monitored for approximately 80 days or until all mice in a treatment group have died.

Example 8

This example describes a study examining UIO-523 toxicology and biodistribution in Syrian hamsters.

Experiments to evaluate the safety and biodistribution of UIO-523 within a single good laboratory practices (GLP) study will be conducted in immunocompetent Syrian hamsters using a dose escalation protocol mimicking a proposed Phase 1 ovarian clinical trial, as shown in Table 1.

Doses ranging from $1 \times 10^9$ to $1 \times 10^{11}$ vp/hamster of UIO-523 will be administered i.p. by a dosing regimen that will mimic an intended clinical trial (e.g., once daily for consecutive days). The highest dose studied will exceed the highest planned human dose by at least 50-fold on a per kg weight basis. The study will be performed in only female animals due to the ovarian indication and will have 5 animals/group/timepoint.

TABLE 1

Overview of Biodistribution/Toxicology Study in Syrian Hamsters

| Group | Treatment (vp/dose) | Dose | Number of Female Hamsters for Necropsy | | |
|---|---|---|---|---|---|
| | | | Day 8 | Day 17 | Day 56 |
| 1 (Control) | Vehicle | 0 | 5F | 5F | 5F |
| 2 (Low-dose) | UIO-523 | $1 \times 10^9$ | 5F | 5F | 5F |
| 4 (Mid-dose) | UIO-523 | $1 \times 10^{10}$ | 5F | 5F | 5F |
| 4 (High-dose) | UIO-523 | $1 \times 10^{11}$ | 5F | 5F | 5F |

The conclusions from this biodistribution/toxicology study will identify the highest dose of virus with a No Observed Adverse Effect Level (NOAEL) that is safe to take into a Phase I study. It will also identify which tissues have the highest level of adenovirus infection following an i.p. administration of the virus and provide a quantitative assessment of the amount of virus particles in each of the infected tissues.

Example 9

This example describes a Phase I clinical trial for the UIO-523 adenovirus in ovarian cancer.

The phase I ovarian cancer (OC) trial will be an open-label, dose-escalating study of UIO-523 as monotherapy and as an adjunct to conventional checkpoint inhibitor (CI) therapy for locally advanced, recurrent, or metastatic ovarian cancer. Approximately 18-30 patients are expected to be enrolled in the study.

Study objectives for the Phase I OC clinical study will be to assess/identify: (1) the safety and feasibility of intraperitoneal (or intravenous) injection of UIO-523 alone and in combination with CI therapy in patients with various regionally advanced and/or metastatic cancer; (2) the site-specific maximum tolerated dose (MTD) as well as recommended Phase II dose of UIO-523 and CI in the tumors; (3) the potential effect of the combination of intraperitoneal (or intravenous) injection of UIO-523 and CI on local control; and (4) the ability of UIO-523 to efficiently transfect tumor cells at the site of administration. The primary endpoint for the Phase I/II study would be tumor response and surgical outcome.

A Phase I/II clinical trial testing UIO-523 is under consideration for the following solid tumors and cancers: esophageal, prostate, glioblastoma, head and neck cancer, hepatocellular carcinoma, bladder cancer, melanoma, colorectal cancer and osteosarcoma: Treatment of esophageal cancer with UIO-523 in combination with CI treatment (e.g. PD-1/PD-L1 inhibitors) as a first line toward tumor reduction in patients with inoperable cancer is attractive due to accessibility of the tumor and the poor prognosis of this cancer. Prostate cancer is another likely indication due to the feasibility of using a direct injection technique, co-administration with brachy therapy, and the existence of the surrogate marker, PSA. Glioblastoma is a likely indication due to the limited treatment options available for affected patients.

UIO-523 will be administered in small volume (2-5 cc) for solid tumors or larger volume (100 cc) for OC as an intratumoral or intraperitoneal injectable solution. The product will be administered by direct injection into the tumor or into the peritoneum at multiple sites (e.g., 2-5 injections for solid tumors, three injections for OC), with a defined geometry of injection. The OC Phase I study will consist of five dose levels ($1 \times 10^{10}$ to $1 \times 10^{12}$ vp, 3 times) with half-log escalations between cohorts. Three patients will be enrolled per dose level. In the event of a dose limiting toxicity, an additional three patients will be enrolled at that dose before the study is allowed to advance to the next dose level. A similar dose escalation design will be used for the Phase I solid tumor study.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A serotype 5 adenovirus or adenoviral vector comprising:
 (a) a nucleic acid sequence encoding a mutant E1A protein operatively linked to a first promoter that is responsive to hypoxia and inflammation,
 (b) a deletion of all or part of the E1B region of the adenoviral genome,
 (c) one or more non-native nucleic acid sequences, each of which encodes an immune modulator and is operatively linked to a second promoter that is active in tumor cells, and
 (d) a fiber protein comprising a serotype 3 adenovirus fiber knob domain.

2. The adenovirus or adenoviral vector of claim 1, which comprises a deletion of all or part of the E3 region of the adenoviral genome and or all or part of the E4 region of the adenoviral genome.

3. The adenovirus or adenoviral vector of claim 2, wherein the one or more non-native nucleic acid sequences are located in the deleted E1B, E3, and/or E4 regions of the adenoviral genome.

4. The adenovirus or adenoviral vector of claim 3, wherein the one or more non-native nucleic acid sequences are located in the deleted E1B region.

5. The adenovirus or adenoviral vector of claim 1, wherein the nucleic acid sequence encoding a mutant E1A protein comprises a deletion of 15 nucleotides within a retinoblastoma (Rb) protein binding region of the E1A protein.

6. The adenovirus or adenoviral vector of claim 1, wherein the first promoter is a secreted protein acidic and rich in cysteine (SPARC) promoter which comprises one or more hypoxia-responsive elements (HREs) and one or more nuclear factor kappa B (NF-κB) inflammation responsive elements (κBRE).

7. The adenovirus or adenoviral vector of claim 1, comprising an exogenous nucleic acid sequence encoding CD40 ligand (CD40L) and an exogenous nucleic acid sequence encoding 4-1BB ligand (4-1BBL).

8. The adenovirus or adenoviral vector of claim 1, wherein the second promoter is a human telomerase reverse transcriptase (hTERT) promoter.

9. A serotype 5 adenovirus or adenoviral vector comprising:
 (a) a nucleic acid sequence encoding a mutant E1A protein operatively linked to a secreted protein acidic and rich in cysteine (SPARC) promoter which comprises one or more hypoxia-responsive elements (HREs) and one or more nuclear factor kappa B (NF-κB) inflammation responsive elements (κBRE),
 (b) a deletion of all or part of the E1B region of the adenoviral genome,
 (c) a first exogenous nucleic acid sequence encoding CD40 ligand (CD40L) and a second exogenous nucleic acid sequence encoding 4-1BB ligand (4-1BBL), wherein the first and second exogenous nucleic acid sequences are (i) separated by an internal ribosome entry site (IRES) and (ii) operatively linked to a human telomerase reverse transcriptase (hTERT) promoter, and
 (d) a fiber protein comprising a single chain camelid antibody amino acid sequence replacing the fiber knob, wherein the camelid antibody specifically binds to the CD276 protein.

10. A composition comprising the adenovirus or adenoviral vector of claim 1 and a pharmaceutically acceptable carrier.

11. The composition of claim 10, which comprises about $1 \times 10^9$ to about $1 \times 10^{14}$ viral particles (vp) of the adenovirus or adenoviral vector.

12. The composition of claim 11, which comprises about $1 \times 10^{10}$ to about $1 \times 10^{12}$ vp of the adenovirus or adenoviral vector.

13. A method of inducing cytotoxicity in tumor cells which comprises contacting tumor cells with the composition of claim 10, whereupon the mutant E1A protein and the exogenous nucleic acid sequences are expressed in the tumor cells and cytotoxicity is induced.

14. The method of claim 13, wherein the tumor cells are in vitro.

15. The method of claim 13, wherein the tumor cells are in vivo.

16. The method of claim 15, wherein the tumor cells are in a mammal.

17. The method of claim 16, wherein the mammal is a human.

18. The method of claim 13, wherein the tumor cells are ovarian cells.

19. The method of claim 13, further comprising treating the tumor cells with a chemotherapeutic agent.

20. The method of claim 13, further comprising treating the tumor cells with a cytokine or checkpoint inhibitor (CI).

* * * * *

SEQUENCE LISTING

<160> NUMBER OF SEQ ID NOS: 4

<210> SEQ ID NO 1
<211> LENGTH: 971
<212> TYPE: DNA
<213> ORGANISM: Human adenovirus

<400> SEQUENCE: 1

```
atgagacata ttatctgcca cggaggtgtt attaccgaag aaatggccgc cagtcttttg      60
gaccagctga tcgaagaggt actggctgat aatcttccac ctcctagcca ttttgaacca     120
cctacccttc acgaactgta tgatttagac gtgacggccc ccgaagatcc caacgaggag     180
gcggtttcgc agattttttcc cgactctgta atgttggcgg tgcaggaagg gattgactta    240
ctcacttttc cgccggcgcc cggttctccg gagccgcctc acctttcccg gcagcccgag     300
cagccggagc agagagcctt gggtccggtt tctatgccaa accttgtacc ggaggtgatc     360
gatcttggct ttccacccag tgacgacgag gatgaagagg gtgaggagtt tgtgttagat     420
tatgtggagc accccgggca cggttgcagg tcttgtcatt atcaccggag gaatacgggg     480
gacccagata ttatgtgttc gctttgctat atgaggacct gtggcatgtt tgtctacagt     540
aagtgaaaat tatgggcagt gggtgataga gtggtgggtt tggtgtggta attttttttt     600 taattttttac agttttgtgg tttaaagaat tttgtattgt gattttttta aaaggtcctg    660
tgtctgaacc tgagcctgag cccgagccag aaccggagcc tgcaagacct acccgccgtc    720
ctaaaatggc gcctgctatc ctgagacgcc cgacatcacc tgtgtctaga gaatgcaata    780
gtagtacgga tagctgtgac tccggtcctt ctaacacacc tcctgagata cacccggtgg    840
tcccgctgtg ccccattaaa ccagttgccg tgagagttgg tgggcgtcgc caggctgtgg    900
aatgtatcga ggacttgctt aacgagcctg ggcaaccttt ggacttgagc tgtaaacgcc    960
ccaggccata a                                                         971
```

<210> SEQ ID NO 2
<211> LENGTH: 5
<212> TYPE: PRT
<213> ORGANISM: Artificial sequence
<220> FEATURE:
<223> OTHER INFORMATION: Synthetic

<400> SEQUENCE: 2

Cys Arg Gly Asp Cys
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic
<220> FEATURE:

```
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 3

Cys Xaa Cys Arg Gly Asp Cys Xaa Cys
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic

<400> SEQUENCE: 4

Cys Asp Cys Arg Gly Asp Cys Phe Cys
1               5
```